US011686792B2

(12) United States Patent
Sodickson et al.

(10) Patent No.: US 11,686,792 B2
(45) Date of Patent: Jun. 27, 2023

(54) RECEIVE COIL ARRANGEMENT AND METHOD FOR USE THEREOF

(71) Applicant: New York University, New York, NY (US)

(72) Inventors: Daniel K. Sodickson, Larchmont, NY (US); Martijn Cloos, New York, NY (US); Bei Zhang, Hartsdale, NY (US)

(73) Assignee: NEW YORK UNIVERSITY, New York, NY (US)

( * ) Notice: Subject to any disclaimer, the term of this patent is extended or adjusted under 35 U.S.C. 154(b) by 467 days.

(21) Appl. No.: 15/966,827

(22) Filed: Apr. 30, 2018

(65) Prior Publication Data

US 2018/0329005 A1    Nov. 15, 2018

Related U.S. Application Data

(60) Provisional application No. 62/541,521, filed on Aug. 4, 2017, provisional application No. 62/492,267, filed on Apr. 30, 2017.

(51) Int. Cl.
*G01R 33/36*     (2006.01)
*G01R 33/34*     (2006.01)
(Continued)

(52) U.S. Cl.
CPC .......... *G01R 33/3614* (2013.01); *A61B 5/055* (2013.01); *A61B 5/6803* (2013.01);
(Continued)

(58) Field of Classification Search
CPC ............ G01R 33/3657; G01R 33/3671; G01R 33/3678; G01R 33/365; G01R 33/3621;
(Continued)

(56) References Cited

U.S. PATENT DOCUMENTS 4,083,006 A * 4/1978 Yokoshima ............ G01R 29/00
343/703
4,605,899 A * 8/1986 Eumurian ............ G01R 33/028
174/396

(Continued)

OTHER PUBLICATIONS

Fujita, Hiroyuki et al. J. Magn. Reson. Imaging 2013;38:12-25 (Year: 2013).*

(Continued)

*Primary Examiner* — Amelie R Davis
*Assistant Examiner* — Helene Bor
(74) *Attorney, Agent, or Firm* — Hunton Andrews Kurth LLP

(57) ABSTRACT

An exemplary coil arrangement can be provided, which can include, for example, coil element(s) having a parallel resonant circuit at a port, where the coil element(s) is detuned by causing a low impedance at the port. Preamplifier arrangements can provide a low impedance at the port of the coil element(s) to suppress the induced current on the coil element(s) thereby reducing the inductive coupling to neighboring element(s). The coil element(s) can include an inductance and a capacitance which cancel each other out. The inductance and the capacitance can cancel each other out such that an impedance of the coil element has no imaginary part at a working frequency. An impedance of the coil element(s) in free space includes a real part that can be greater than a sum of losses for the coil element(s).

24 Claims, 39 Drawing Sheets

(51) Int. Cl.
A61B 5/00 (2006.01)
A61B 5/055 (2006.01)
G01R 33/3415 (2006.01)

(52) U.S. Cl.
CPC ...... *A61B 5/6806* (2013.01); *G01R 33/34007* (2013.01); *G01R 33/3415* (2013.01); *G01R 33/34084* (2013.01); *G01R 33/365* (2013.01); *G01R 33/3621* (2013.01); *G01R 33/3657* (2013.01)

(58) Field of Classification Search
CPC .............. G01R 33/3415; G01R 33/343; G01R 33/34084; G01R 33/3607; G01R 33/3614; G01R 33/3628; G01R 33/3642; G01R 33/3635; G01R 33/34007; A61B 5/6803; A61B 5/055; A61B 5/6806
See application file for complete search history.

(56) References Cited

U.S. PATENT DOCUMENTS

| | | | | |
|---|---|---|---|---|
| 4,775,837 | A * | 10/1988 | Roschmann | G01R 33/3628 324/318 |
| 4,839,594 | A * | 6/1989 | Misic | G01R 33/34046 324/318 |
| 6,094,599 | A * | 7/2000 | Bingham | A61N 1/0484 607/149 |
| 6,850,067 | B1 | 2/2005 | Burl et al. | |
| 6,980,000 | B2 * | 12/2005 | Wong | G01R 33/34053 324/318 |
| 2003/0146750 | A1 * | 8/2003 | Vaughan, Jr. | G01R 33/34046 324/318 |
| 2006/0244448 | A1 * | 11/2006 | Ballon | G01R 33/3678 324/318 |
| 2008/0275332 | A1 * | 11/2008 | Alradady | G01R 33/34076 600/422 |
| 2010/0182009 | A1 * | 7/2010 | Crozier | G01R 33/365 324/322 |
| 2013/0063147 | A1 * | 3/2013 | Findeklee | G01R 33/365 324/309 |
| 2013/0093425 | A1 * | 4/2013 | Chu | G01R 33/365 324/318 |
| 2014/0197832 | A1 * | 7/2014 | Driesel | H01Q 7/04 324/307 |
| 2018/0081007 | A1 * | 3/2018 | Stormont | G01R 33/34007 |

OTHER PUBLICATIONS

Bloch, F. et al., "Quantitative Determination of the Magnetic Moment of the Neutron in Units of the Proton Moment," Phys. Rev., vol. 74, No. 9, pp. 1025-1045, Nov. 1, 1948.
Lauterber, Paul C., "Image Formation by Induced Local Interactions: Examples Employing Nuclear Magnetic Resonance," Nature, vol. 242, pp. 190-191, 1973.
Mansfield, P. et al. "NMR 'Diffraction' in Solids?," Phys. C. Solid. Stat., pp. L422-L426, 1973.
Roemer, P.B. et al., "The NMR Phased Array," Magn. Reson. Med., vol. 16, pp. 192-225, 1990.
Wang, Jianmin et al., "Calculation of the Signal-to-Noise Ratio for Simple Surface Coils and Arrays of Coils," IEEE Trans. Biomed. Eng., vol. 42, pp. 908-917, Sep. 1995.
Ocali, Ogan et al., "Ultimate Intrinsic Signal-to-Noise Ratio in MRI," Magn. Reson. Med., vol. 39, pp. 462-473, 1998.
Schnell, Wilfried et al., "Ultimate Signal-to-Noise Ratio of Surface and Body Antennas for Magnetic Resonance Imaging," IEEE Trans. Antennas. Propag., vol. 48, pp. 418-428, Mar. 2000.
Ohliger, Michael A. et al., "Ultimate Intrinsic Signal-to-Noise Ratio for Parallel MRI: Electromaganetic Field Considerations," Magn. Reson. Med., vol. 50, pp. 1018-1030, 2003.
Wiesinger, Florian et al., "Electrodynamics and Ultimate SNR in Parallel MR Imaging," Magn. Reson. Med., vol. 52, pp. 376-390, 2004.
Lattanzi, Riccardo et al., "Performance Evaluation of a 32-Element Head Array with Respect to the Ultimate Intrinsic SNR," NMR Biomed vol. 23, pp. 142-151, Jan. 29, 2009.
Lattanzi, Riccardo et al., "Ideal Current Patterns Yielding Optimal Signal-to-Noise Ratio and Specific Absorption Rate in Magnetic Resonance Imaging: Computational Methods and Physical Insights," Magn. Reson. Med., vol. 68, pp. 286-304, Jul. 2012.
Wiggins, Graham C. et al., "96-Channel Receive-Only Head Coil for 3 Tesla: Design Optimization and Evaluation," Magn. Reson. Med., vol. 62, pp. 754-762, Sep. 2009.
Schmitt, Melanie et al., "A 128-Channel Receive-Only Cardiac Coil for Highly Accelerated Cardiac MRI at 3 Tesla," Magn. Reson. Med., vol. 59, pp. 1431-1439, Jun. 2008.
Fujita, Hitoyuki et al., "RF Surface Receive Array Coils: The Art of an LC Circuit," J. Magn. Reson. Imaging, vol. 38, pp. 12-25, 2013.
Kurs, Andre et al., "Wireless Power Transfer via Strongly Coupled Magnetic Resonances," Science, vol. 317, pp. 83-86, Jul. 6, 2007.
Tierney, Brian et al., "Planar Shielded-Loop Resonators for Wireless Non-Radiative Power Transfer," IEEE Antennas and Propagation Society International Symposium (APSURSI), pp. 842-843, 2014.
Gonord, P. et al., "Parallel-Plate Split-Conductor Surface Coil: Analysis and Design," Magn. Reson. Med., vol. 6, pp. 353-358, 1988.
Serfaty, Stephane et al., "Multi-Turn Split-Conductor Transmission-Line Resonators," Magn. Reson. Med. vol. 38, pp. 687-689, 1997.
Frass-Kriegl, Roberta et al., "Multi-turn Multi-Gap Transmission Line Resonators—Concept, Design and First Implementation at 4.7T and 7T," J. Magn. Reson. vol. 273, pp. 65-72, 2016.
Corea, Joseph R. et al., "Screen-Printed Flexible MRI Receive Coils," Nat. Commun., vol. 7, pp. 1-7, 2016.
Vasanawala, Shreyas S. "Development and Clinical Implementation of Very Light Weight and Highly Flexible AIR Technology Arrays," Proc. Intl. Soc. Mag. Reson. Med., pp. 1-22, 2017.
Stromont, Robert et al., "Reimagining Flexible Coil Technology," SIGNA, Spring, pp. 69-71, 2017.
Stensgaard, Anders, "Planar Quadrature Coil Design Using Shielded-Loop Resonators," J. Magn. Reson., vol. 125, pp. 84-91, 1997.
Sodickson, Daniel K. et al., "Simultaneous Acquisition of Spatial Harmonics (SMASH): Fast Imaging with Radiofrequency Coil Arrays," Magn. Reson. Med., vol. 38, pp. 591-603, 1997.
Pruessmann, Klaas P. et al., "SENSE: Sensitivity Encoding for Fast MRI," Magn. Reson. Med., vol. 42, pp. 952-962, 1999.
Griswold, Mark A. et al., "Generalized Autocalibrating Partially Parallel Acquisitions (GRAPPA)," Magn. Reson. Med., vol. 47, pp. 1202-1210, 2002.
Larkman, David J. et al., "Use of Multicoil Arrays for Separation of Signal from Multiple Slices Simultaneously Excited," J Magn. Reson. Imaging. vol. 13, No. 2, pp. 313-317, 2001.
Setsompop, Kawin et al., "Blipped-Controlled Aliasing in Parallel Imaging for Simultaneous Multislice Echo Planar Imaging with Reduced G-Factor Penalty," Magn. Reson. Med., vol. 67, pp. 1210-1224, May 2012.
Schnall, M.D. et al., "A New Double-Tuned Probed for Concurrent 1H and 31P NMR," J. Magn Reson. vol. 65, pp. 122-129, 1985.
Avdievich, N.I. et al., "4 T Actively Detuneable Double-Tuned 1H/31P Head Volume Coil and Four-Channel 31P Phased Array for Human Brain Spectroscopy," J Magn Reson. vol. 186, pp. 341-346, Jun. 2007.
Brown, Ryan et al., "Design of a Nested Eight-Channel Sodium and Four-Channel Proton Coil for 7T Knee Imaging," Magn. Reson. Med., vol. 70, pp. 259-268, Jul. 2013.
Shajan, G. et al., "Three-Layered Radio Frequency Coil Arrangement for Sodium MRI of the Human Brain at 9.4 Tesla," Magn. Reson. Med., vol. 75, pp. 906-916, 2016.
Kriegl, Roberta et al., "Novel Inductive Decoupling Technique for Flexible Transceiver Arrays of Monolithic Transmission Line Resonators," Magn. Reson. Med., vol. 73, pp. 1669-1681, 2015.

(56) References Cited

OTHER PUBLICATIONS

Hosseinnezhadian, S. et al., "A Flexible Transceiver Array for 7 T Cardiac MRI: First Imaging Experiments," in Proceedings of the ESMRMB Barcelona, p. 315, 2017.

Keil, Boris et al. "A 64-Channel 3T Array Coil for Accelerated Brain MRI," Magn. Reson. Med. vol. 70, pp. 248-258, 2013.

Noeske, Ralph et al., "Human Cardiac Imaging at 3T Using Phased Array Coils," Magn. Reson. Med. vol. 44, pp. 978-982, 2000.

Chung, Sohae et al., "Rapid B1+ Mapping using a Preconditioning RF Pulse with TurboFLASH Readout," Magn. Reson. Med., vol. 64, pp. 439-446, Aug. 2010.

Kellman, Peter et al., Image reconstruction in SNR units: a general method for SNR measurement. Magn. Reson. Med., 2005;54:1439-1447.

Winkelmann, Stefanie et al., "An Optimal Radial Profile Order Based on the Golden Ratio for Time-Resolved MRI," IEEE Trans. Med. Imaging. vol. 26, pp. 68-76, Jan. 2007.

\* cited by examiner

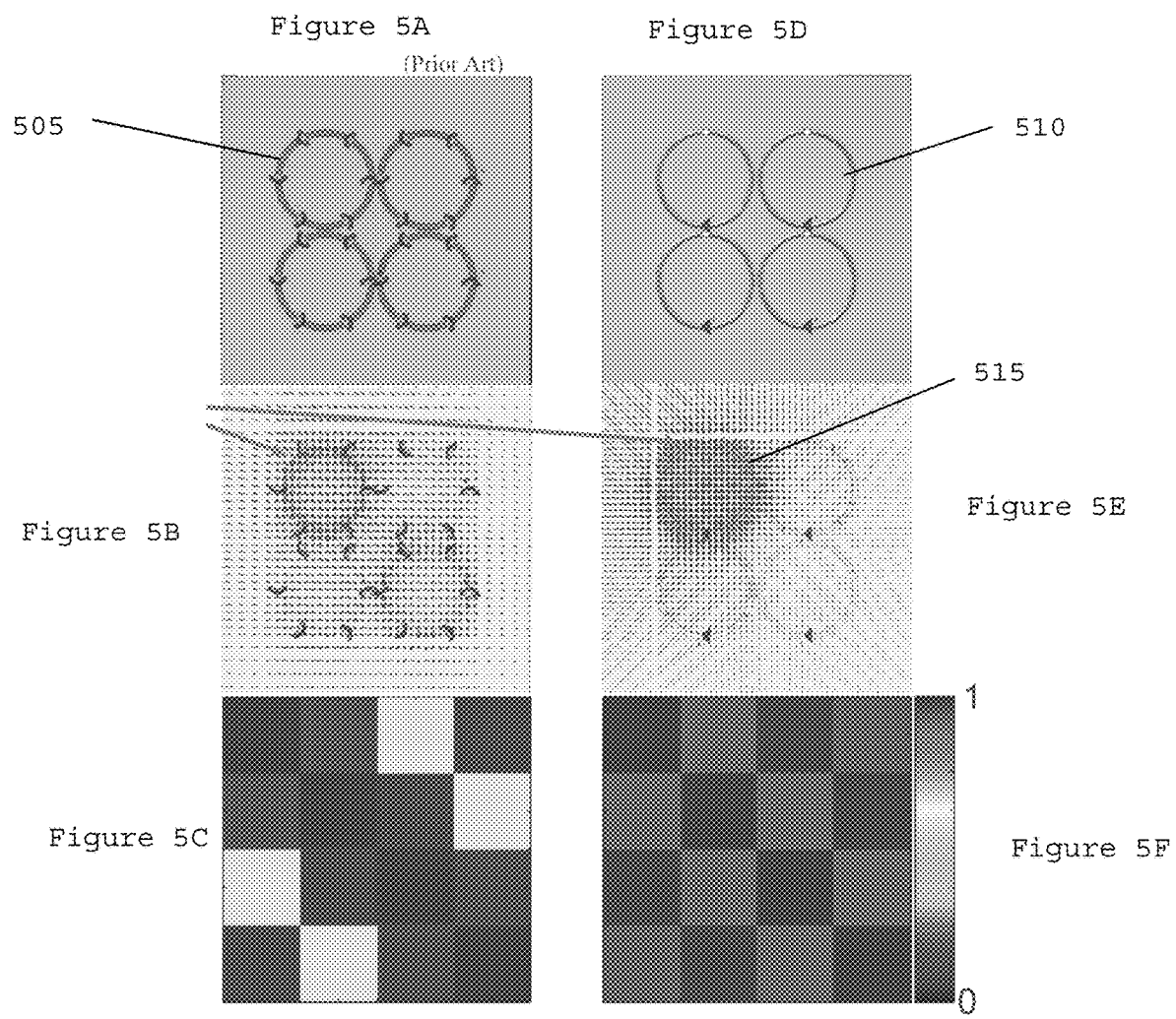

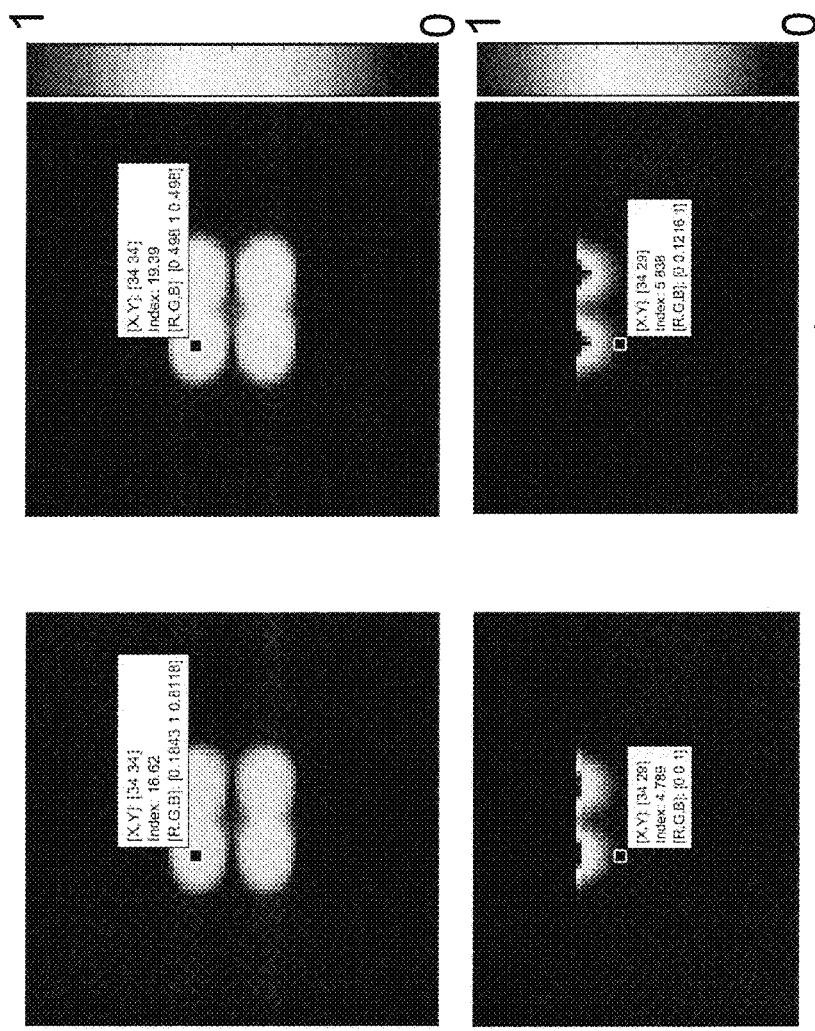

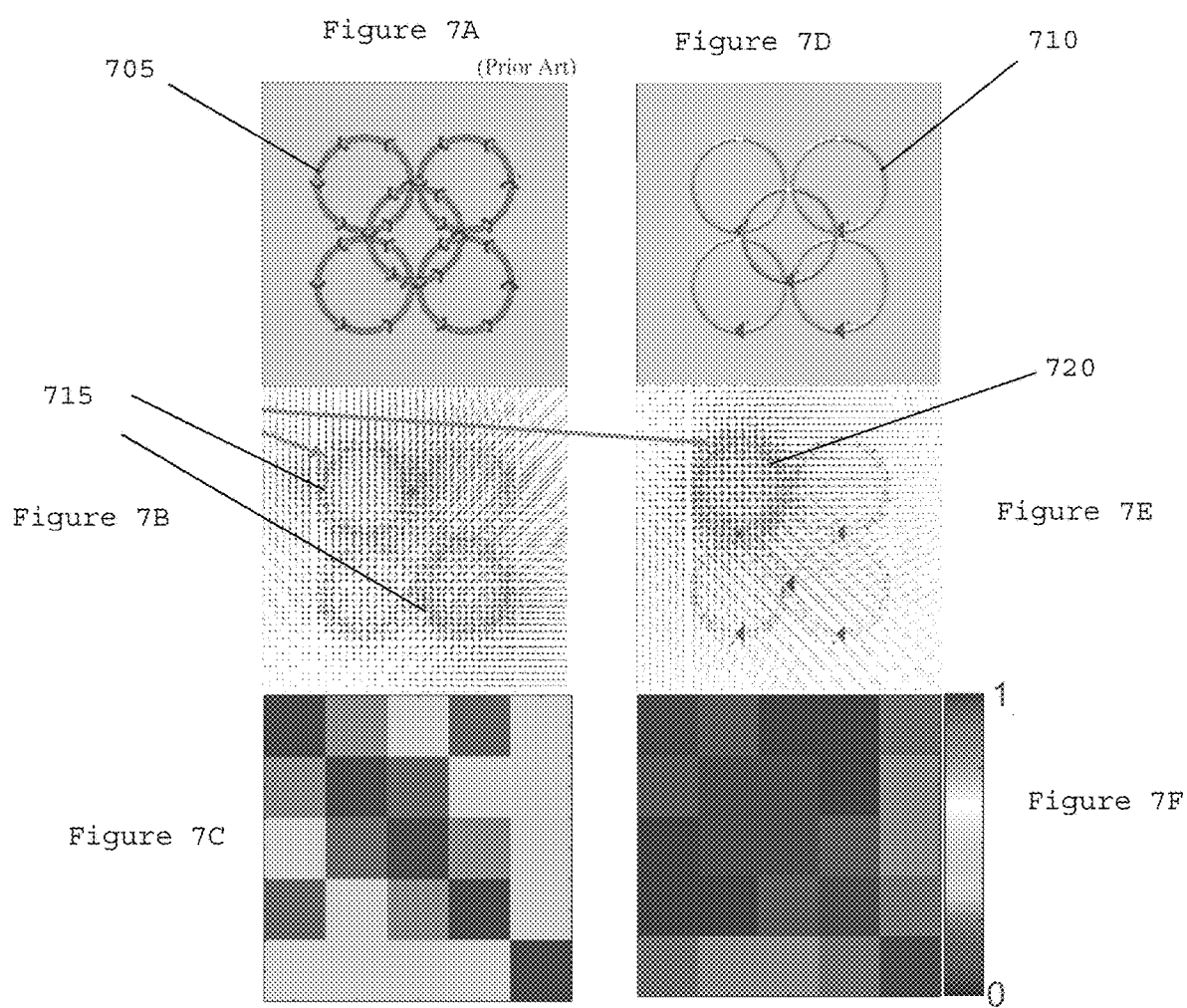

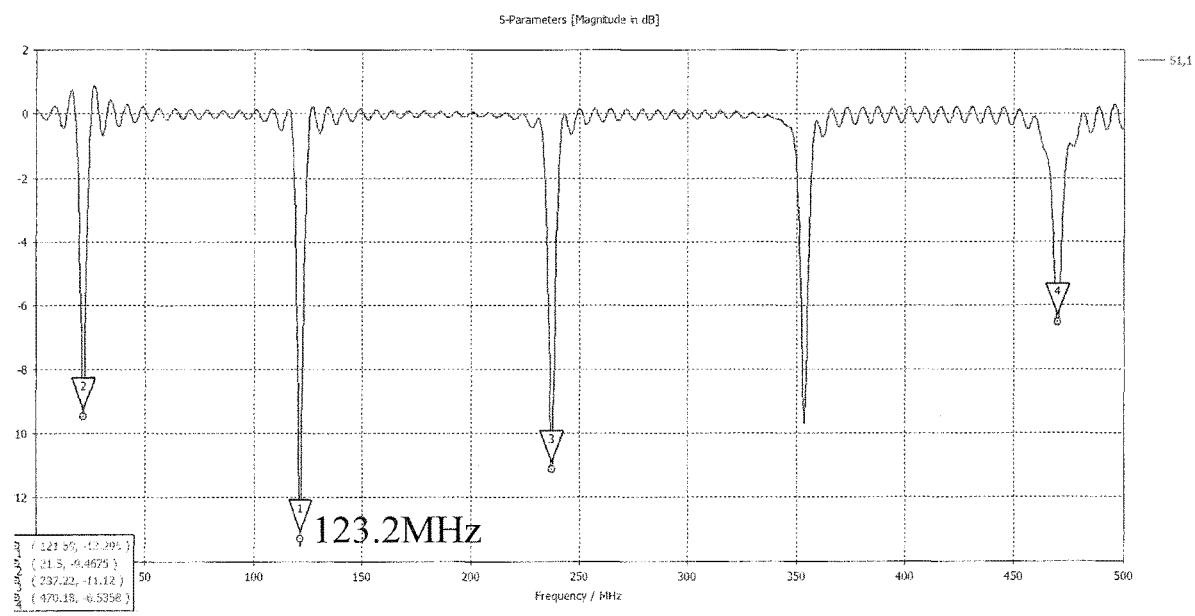
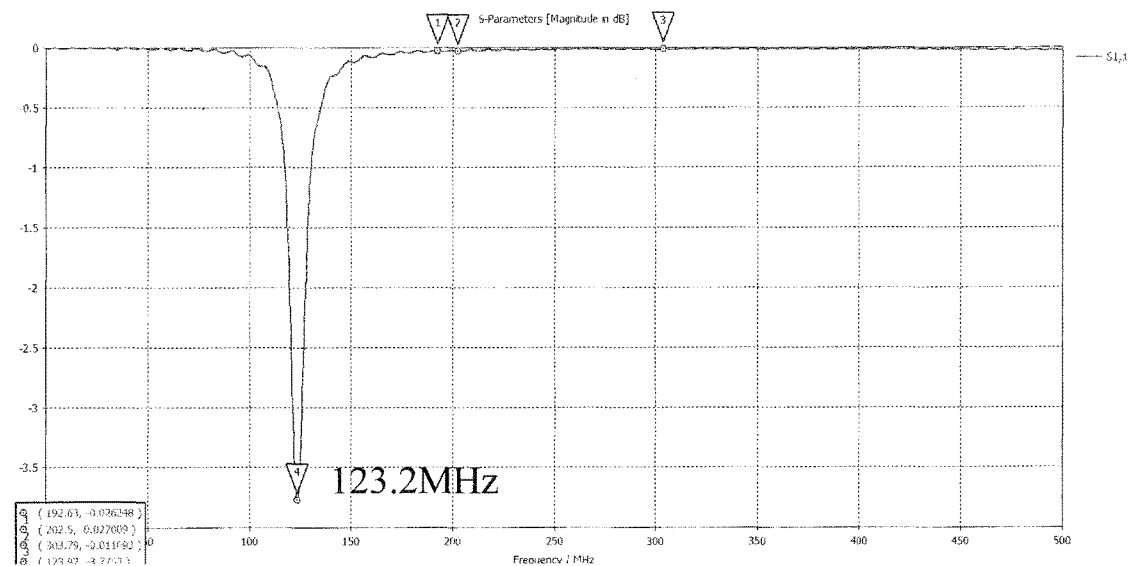
Figure 10

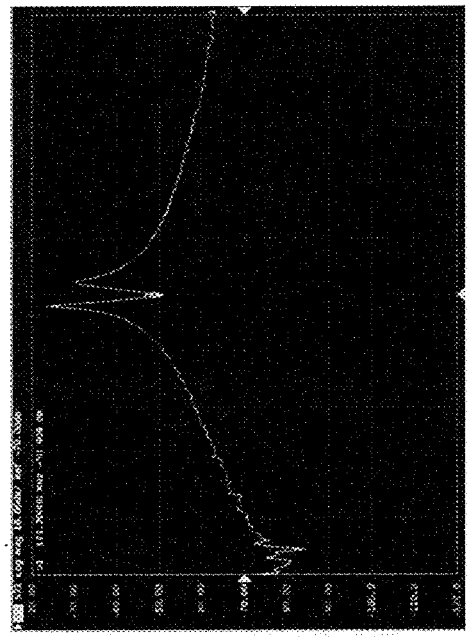
Figure 12A
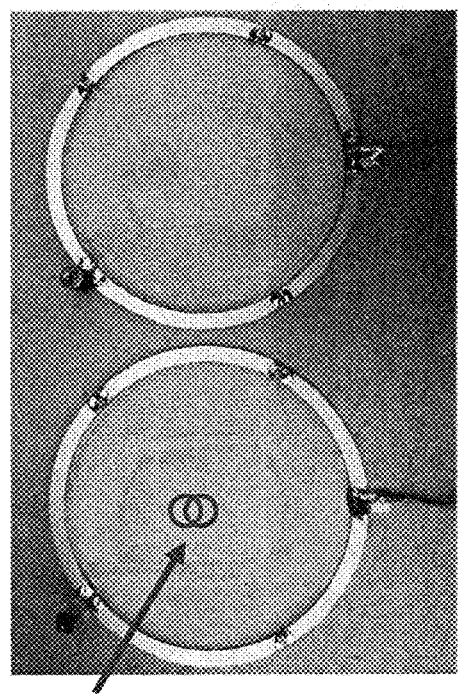
Figure 12B
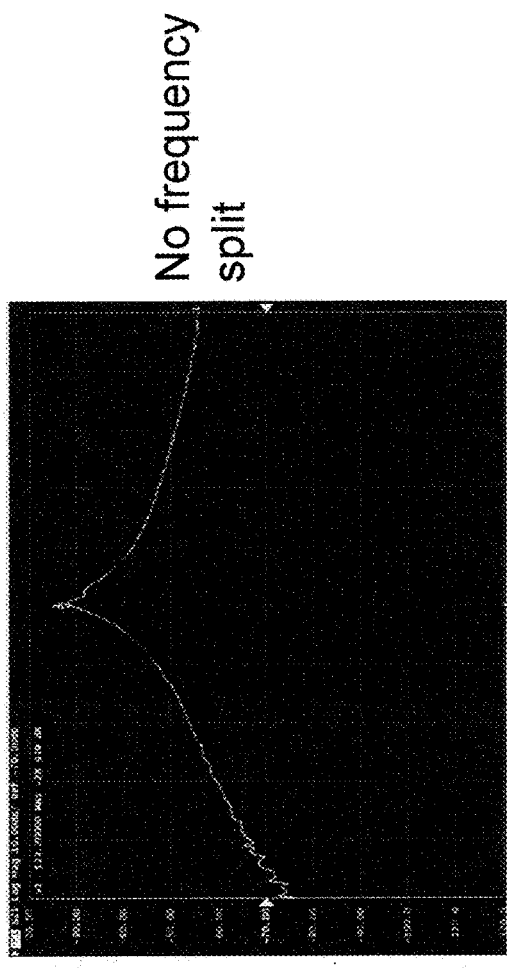
Figure 12C — Strong frequency split
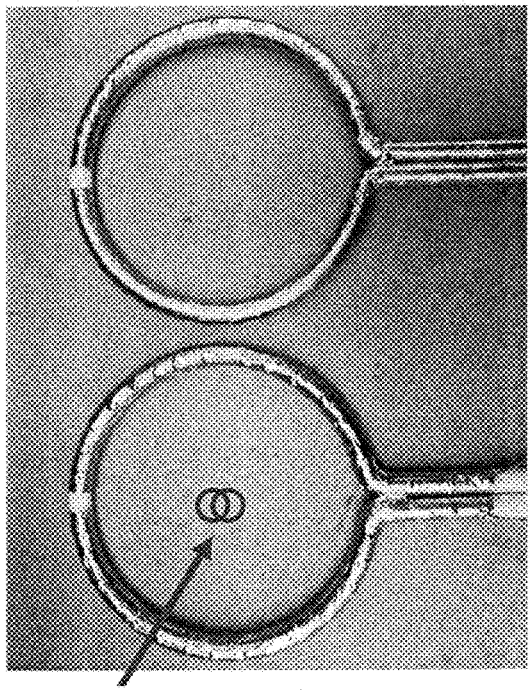
Figure 12D — No frequency split

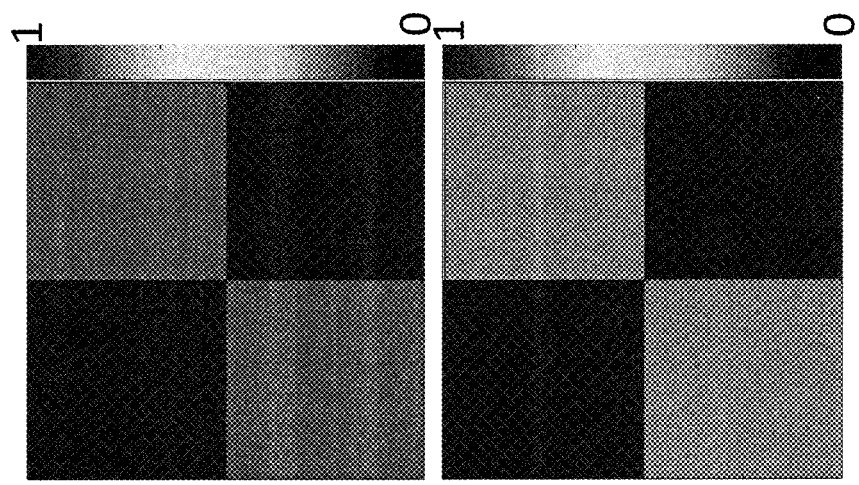
Figure 14B
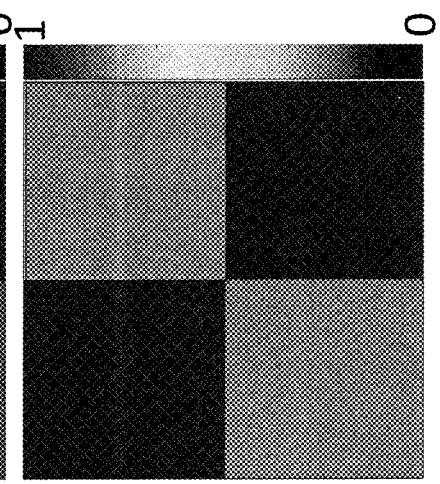
Figure 14D
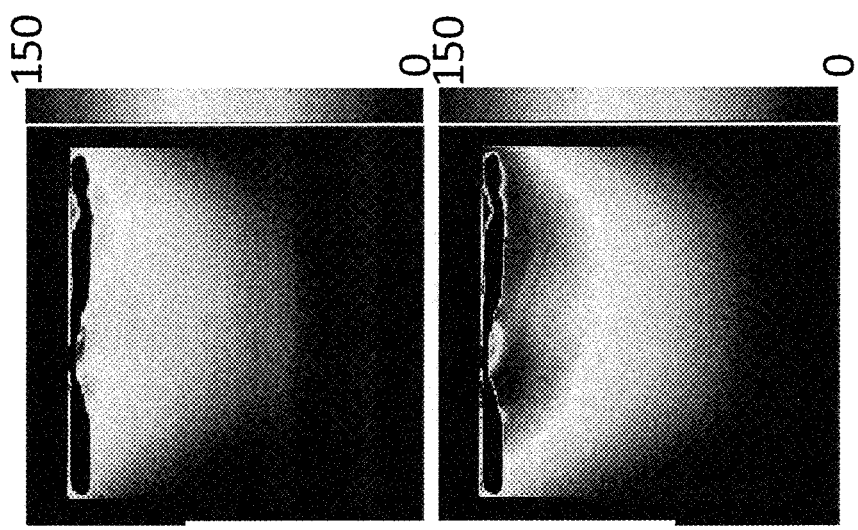
Figure 14A
Figure 14C
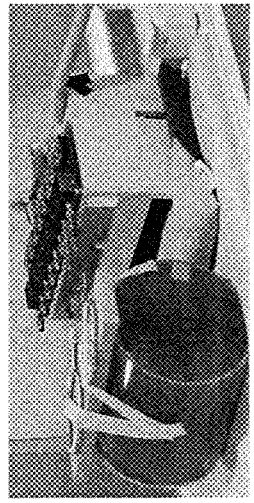
Figure 14E Figure 18A
Prior Art
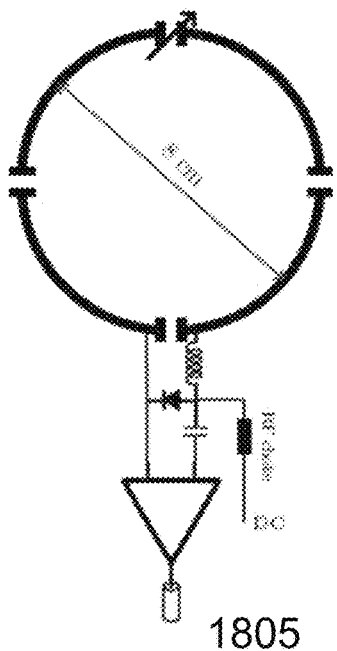
Figure 18B
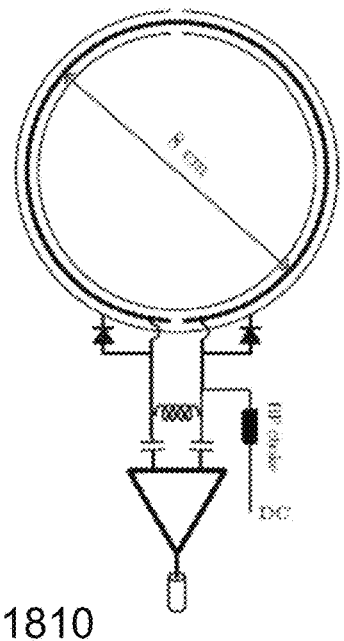
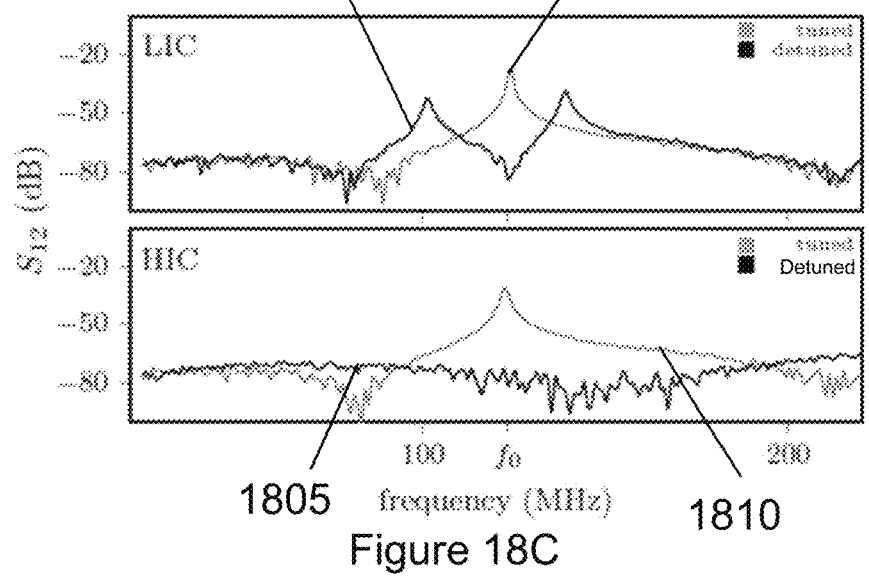
Figure 18C
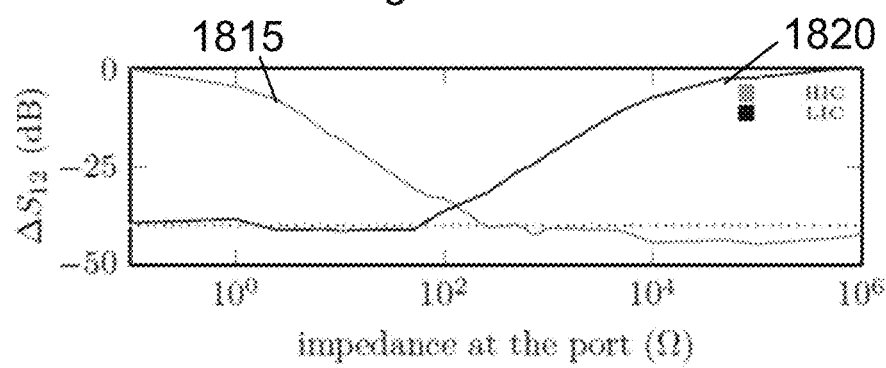
Figure 18D Figure 19A
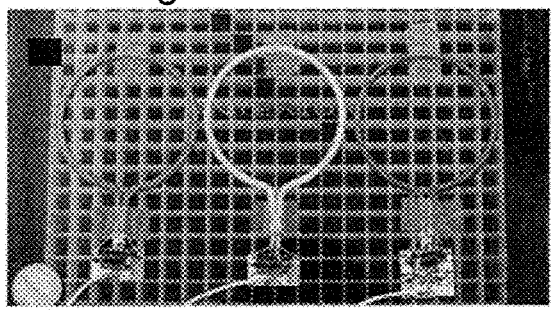
Figure 19B
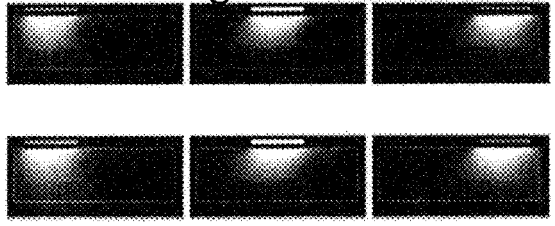
Figure 19C
Figure 19D
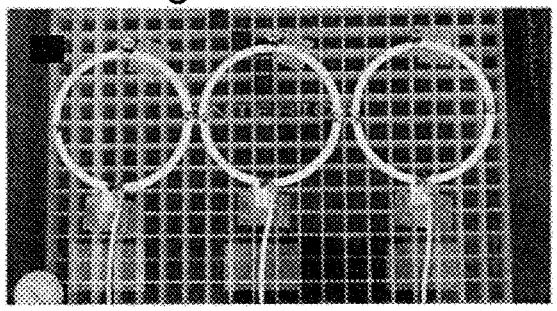
Figure 19E
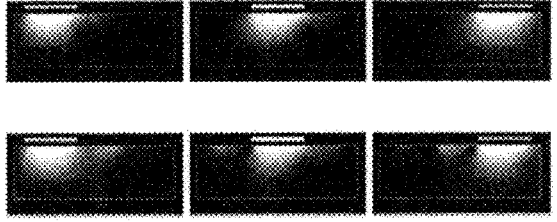
Figure 19F

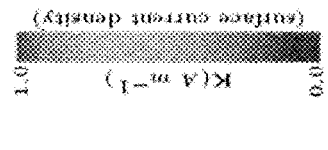
Figure 23C
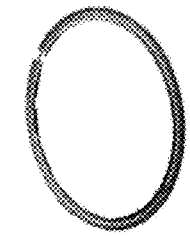
Figure 23B
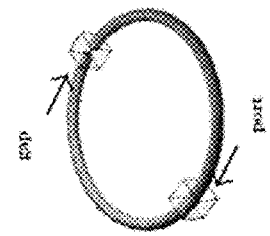
Figure 23A
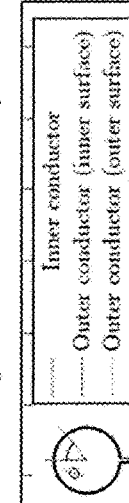
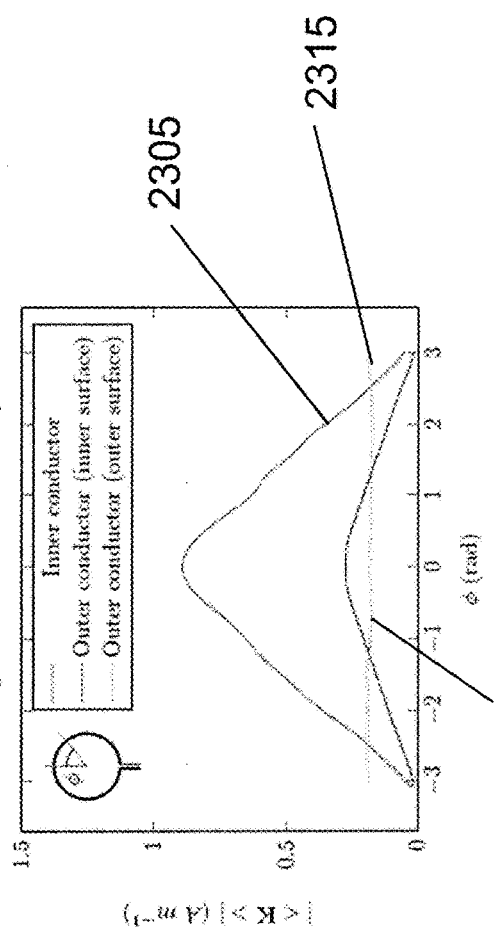
Figure 23F
Figure 23D
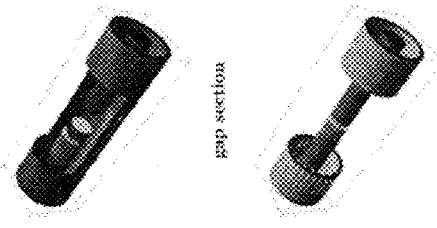
Figure 23E

2905

RECEIVE COIL ARRANGEMENT AND METHOD FOR USE THEREOF

CROSS-REFERENCE TO RELATED APPLICATION(S)

This application relates to and claims priority from U.S. Patent Application No. 62/492,267, filed on Apr. 30, 2017 and U.S. Patent Application No. 62/541,521, filed on Aug. 4, 2017, the entire disclosures of which are incorporated herein by reference.

FIELD OF THE DISCLOSURE

The present disclosure relates generally to a coil arrangement, and more specifically, to exemplary embodiments of an exemplary receive coil arrangement and method for use thereof.

BACKGROUND INFORMATION

When a substance, such as a human tissue, is subjected to a uniform static magnetic field (e.g., polarizing field B0), the individual magnetic moments of the spins in the tissue attempt to align with this polarizing field, but precess about it in random order at their characteristic Larmor frequency. If the substance or tissue is subjected to a time-varying magnetic field (e.g., excitation field B1) which is in the x-y plane and which is near the Larmor frequency, the net aligned moment, Mz, may be rotated, or "tipped", into the x-y plane to produce a net transverse magnetic moment Mt. A signal is emitted by the excited spins, and this signal may be received and processed to form an image.

When utilizing these signals to produce images, magnetic field gradients (Gx, Gy, and Gz) are employed. Typically, the region to be imaged is scanned by a sequence of measurement cycles in which these gradients vary according to the particular localization method being used. The resulting set of received nuclear magnetic resonance ("NMR") signals are digitized and processed to reconstruct the image using one of many well-known reconstruction techniques.

The NMR signals are detected using an RF antenna in the form of one or more RE coils. Magnetic resonance imaging ("MRI") systems can include a whole-body RE coil that can receive NMR signals emanating from anywhere in a subject being imaged, but it is also common practice to use specially designed local radio frequency ("RF") coils when imaging specific anatomy. These local coils are positioned very close to the anatomy being imaged, and the result is an increased sensitivity to the NMR signals, and a consequent higher signal-to-noise ratio ("SNR") in the image reconstructed from those signals.

While single element local coils are used in some clinical applications, because of their limited receptivity field, it is also common practice to employ multi-element RF coil arrays. Each coil element operates as a separate RF antenna, and is connected to a separate receive channel in the MRI system. The separate NMR signals are combined to increase the receptivity field of view to that of the combined RF coil elements.

Conventional RF receive coil elements generally consist of several conductive segments connected by lumped elements, such as capacitors, to form a LC circuit at the resonant frequency. To extract the signal, a LC impedance transformation circuit is placed at the receiving port of the coil, to match the impedance of the coil to the optimal noise impedance of the preamplifier. This transform is chosen such that, from the viewpoint of the coil, the receive port appears to be an open, infinite, impendence. Thus, the current flowing in the coil is suppressed, minimizing the induced electromagnetic fields close to the coil, which would otherwise couple signal from one coil to the next. In the field of MRI, this is called preamplifier decoupling. (See e.g., Reference 41). In addition to the above-described lumped elements, a PIN diode and inductor are placed in parallel to one or more capacitors. With these elements in place, a DC current can be injected into the coil to render it "transparent" to RF at the resonance frequency of the nuclei of interest. This mechanism circumvents an interaction between the body coil (or other transmit coil) and local receive coils during transmission. Impedance matching and transmit-receive decoupling circuits add complexity to receive coils, and they can also be associated with unwanted noise. Preamplifier decoupling can also be imperfect, resulting in constraints on the geometrical arrangement of elements in RF coil arrays.

Thus, it may be beneficial to provide an exemplary receive coil arrangement which can overcome at least some of the deficiencies described herein above.

SUMMARY OF EXEMPLARY EMBODIMENTS

An exemplary coil arrangement can be provided, which can include, for example, coil element(s) having a parallel resonant circuit at a port, where the coil element(s) is detuned by causing a low impedance at the port. The coil element(s) can include an inductance and a capacitance which cancel each other out. The inductance and the capacitance can cancel each other out such that an impedance of the coil element has no imaginary part at a working frequency. An impedance of the coil element(s) in free space can include a real part that can be greater than a sum of losses for the coil element(s). The coil element(s) can include a loop having a distributed inductance and a distributed capacitance. The distributed inductance and the distributed capacitance can be formed using a coaxial structure. The coaxial structure can include an inner conductor encased in a substrate wrapped with an outer conductor.

In some exemplary embodiments of the present disclosure, the coaxial structure can include a break(s) in the inner conductor and the outer conductor at opposite ends thereof. The coil element(s) can be flexible. A pre-amplifier arrangement can be provided, which can be configured to cause the low impedance at the port. The pre-amplifier arrangement can be configured to suppress currents on the coil element(s). The pre-amplifier arrangement(s) can be configured to reduce inductive coupling with neighboring coil elements. The pre-amplifier(s) arrangement can be configured to reduce the inductive coupling with neighboring coil elements without using a geometrical overlap. The coil element(s) can be integrated into a flexible glove. The coil element(s) can be integrated into a wearable garment. The coil element(s) can be integrated into an adaptive housing that conforms to a shape and a size of a subject being imaged. A pin diode(s) can be configured to create the low impedance at the port.

A method of imaging an anatomical structure(s) can be provided, which can include, for example, providing an element(s) having a parallel resonant circuit at a port, reducing a current(s) on the coil element(s) by providing a low impedance at the port, and imaging the anatomical structure(s) using the at least one coil element. Interaction with neighboring coil element(s) can be eliminated using a pre-amplifier arrangement that can create a low impedance at the port. The coil elements(s) can be detuned using (i) a pre-amplifier arrangement, (ii) a positive-intrinsic-negative (PIN) diode, or (iii) a Microelectromechanic ("MEM") switch. The coil element(s) can be provided in a flexible garment.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 5A and 5B are diagrams illustrating an array of conventional coils;

FIG. 5C is a coil coefficient matrix for the coils shown in FIGS. 5A and 5D;

FIGS. 5D and 5E are exemplary diagrams of an array of the exemplary coils according to an exemplary embodiment of the present disclosure;

FIG. 5F is a coil coefficient matrix for the coils shown in FIGS. 5D and 5E according to an exemplary embodiment of the present disclosure;

FIG. 6A is a diagram and a set of SNR maps for the array of conventional coils;

FIG. 6B is an exemplary diagram and a set of SNR maps for the array of exemplary coils according to an exemplary embodiment of the present disclosure;

FIGS. 7A and 7B are diagrams illustrating a further array of conventional coils;

FIG. 7C is a coil coefficient matrix for the coils shown in FIGS. 7A and 7D;

FIGS. 7D and 7E are exemplary diagrams of a further array of exemplary coils according to an exemplary embodiment of the present disclosure;

FIG. 7F is a coil coefficient matrix for the further coils shown in FIGS. 7D and 7E according to an exemplary embodiment of the present disclosure;

FIG. 10 is a set of graphs illustrating the S parameter for the exemplary coil according to an exemplary embodiment of the present disclosure;

FIGS. 12A and 12B are exemplary images of the exemplary coil according to an exemplary embodiment of the present disclosure;

FIGS. 12C and 12D are related exemplary graphs of the S21 for the exemplary coils shown in FIGS. 12A and 12B, respectively, according to an exemplary embodiment of the present disclosure;

FIGS. 14A and 14B are further exemplary SNR maps and noise coefficient matrix, respectively, for the exemplary array of exemplary coils according to an exemplary embodiment of the present disclosure;

FIGS. 14C and 14D are a further set of SNR maps and noise coefficient matrix, respectively, for a traditional coil;

FIG. 14E is a further exemplary image of the exemplary coil and a traditional coil placed side-by-side on a phantom according to an exemplary embodiment of the present disclosure; e.g.

FIG. 18A is a schematic diagram of a traditional LIC coil;

FIG. 18B is an exemplary schematic of an exemplary HIC coil according to an exemplary embodiment of the present disclosure;

FIG. 18C is a set of graphs of the observed resonances with a double probe experiment according to an exemplary embodiment of the present disclosure;

FIG. 18D is a graph of the induced current measured at the resonance frequency during the double probe experiment of FIG. 18C according to an exemplary embodiment of the present disclosure;

FIG. 19A is an exemplary image of three 8-cm diameter HIC elements according to an exemplary embodiment of the present disclosure;

FIGS. 19B and 19C are exemplary MRI images generated using the exemplary HIC elements from FIG. 19A according to an exemplary embodiment of the present disclosure;

FIG. 19D is an exemplary image of three 8-cm diameter LIC elements;

FIGS. 19E and 19F are MRI images generated using the LIC elements illustrated in FIG. 19D;

FIG. 23A is an exemplary diagram of an inner conductor according to an exemplary embodiment of the present disclosure;

FIG. 23B is an exemplary diagram of a cross-section of the exemplary conductor according to an exemplary embodiment of the present disclosure;

FIG. 23C is an exemplary diagram of an outer conductor according to an exemplary embodiment of the present disclosure;

FIG. 23D is an exemplary diagrams of a port section for the exemplary conductor according to an exemplary embodiment of the present disclosure;

FIG. 23E is an exemplary diagrams of a gap section for the exemplary conductor according to an exemplary embodiment of the present disclosure;

FIG. 23F is an exemplary graph of the average surface current density for the exemplary conductor according to an exemplary embodiment of the present disclosure;

Figure 1:
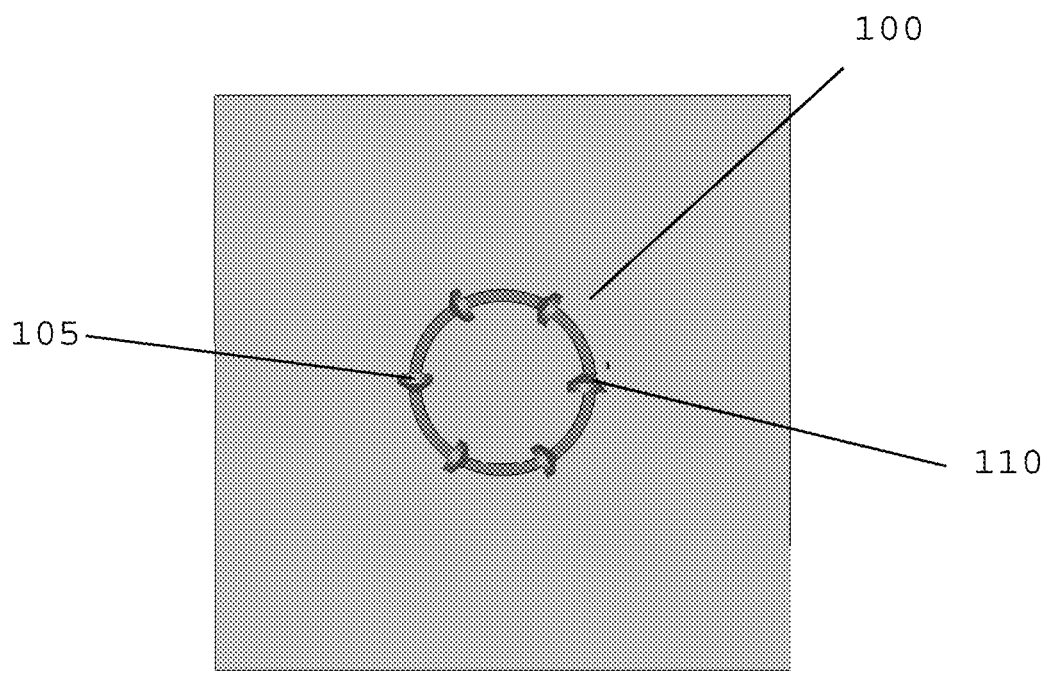
FIG. 1 is a diagram of a conventional coil.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Figure 2:
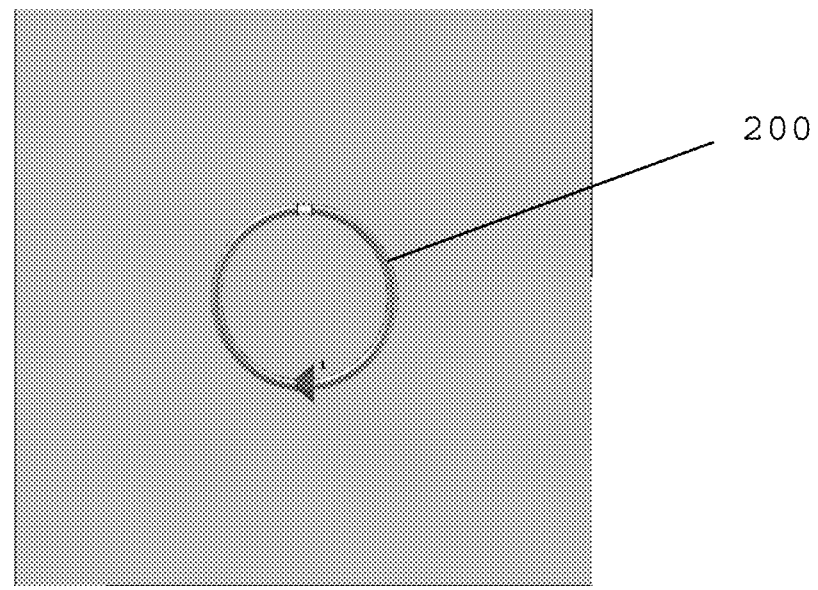
FIG. 2 is a diagram of an exemplary coil according to an exemplary embodiment of the present disclosure.

As shown in FIG. 1, traditional coils can include five tuning capacitors (e.g., tuning capacitors 105) and one matching capacitor 110 to tune and match the coil to the working frequency. In contrast, as shown in FIG. 2, exemplary embodiments of the present disclosure relate to a coil arrangement 200 (e.g., a receive coil arrangement) with a high intrinsic impedance. In-contrast to traditional receive coils that have a low intrinsic impedance. This high impedance prevents current from flowing in the coils, and can reduce inductive coupling between them. This can be accomplished, for example, using an exemplary detuning arrangement. For example, by specifying the diameters of the inner conductor and the outer conductor, and permittivity of the substrate, and also segmenting the outer conductor, coil performance can be optimized at a working frequency, without the need for lumped elements. The diameter of both coils shown in FIGS. 1 and 2 can be about 6 cm, with a width (e.g., diameter) of both coils being about 4 mm.

The exemplary coil arrangement can be used in all nuclei, and can be utilized in multi-nuclei imaging, because the coupling between the coils can be very small. For example, the resonant frequency of phosphorous at 7T (e.g., 120.4 MHz) and the resonant frequency of the proton at 3T (e.g., 123.2 MHz) are close, and the exemplary coil arrangement can be used in these two applications. Further, images of different nuclei produced using the exemplary coil arrangement can be acquired at the same time. The exemplary coil can be used in any case that a MRI receive coil is utilized.

An exemplary measurement for a receive coil can be the SNR. The best possible SNR can be approximated by combining multiple elements into an encircling array. Due to coupling issues between neighboring coil elements, the design of such an array can become a complicated geometrical puzzle. Prior solutions to this problem implemented a soccer ball geometry for the head and the loop dipole structure for the body. However, such structures can present problems during imaging. For example, for a given head size, the soccer ball geometry can approximate the best possible intrinsic SNR quite well. However, it would be beneficial to use a smaller coil for a neonatal brain as compared to an adult. This problem has led to various solutions, such as size adaptable coils like a trellis based design.

Figure 3:
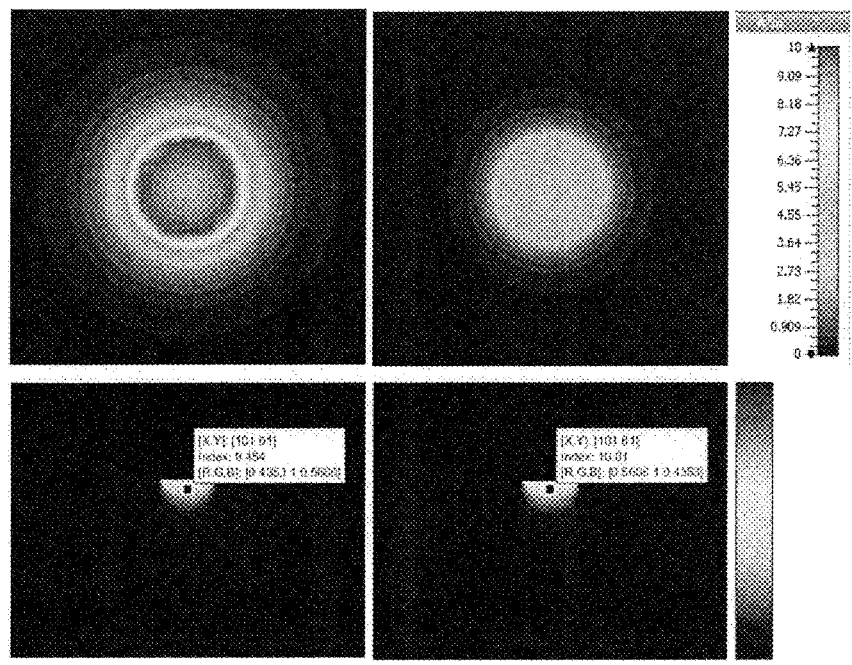
FIG. 3A is an exemplary SNR map for a conventional coil.
FIG. 3B is an exemplary SNR map for the exemplary coil design according to an exemplary embodiment of the present disclosure.

FIG. 3A shows SNR maps for a conventional coil and FIG. 3B shows SNR maps for the exemplary coil design according to an exemplary embodiment of the present disclosure. Small currents can be seen on the exemplary coil, with a low induced magnetic (H) field, as well as a low electric (E) field, (e.g., with the absolute magnitude squared of the E field integrated against the conductivity σ of the body corresponding to noise produced by the body). However, the current is evenly distributed on the coil with no local effect in the H field. As shown in FIG. 3B, even with loss taken into account, the SNR of the exemplary coil is better than the traditional coil.

Figure 4:
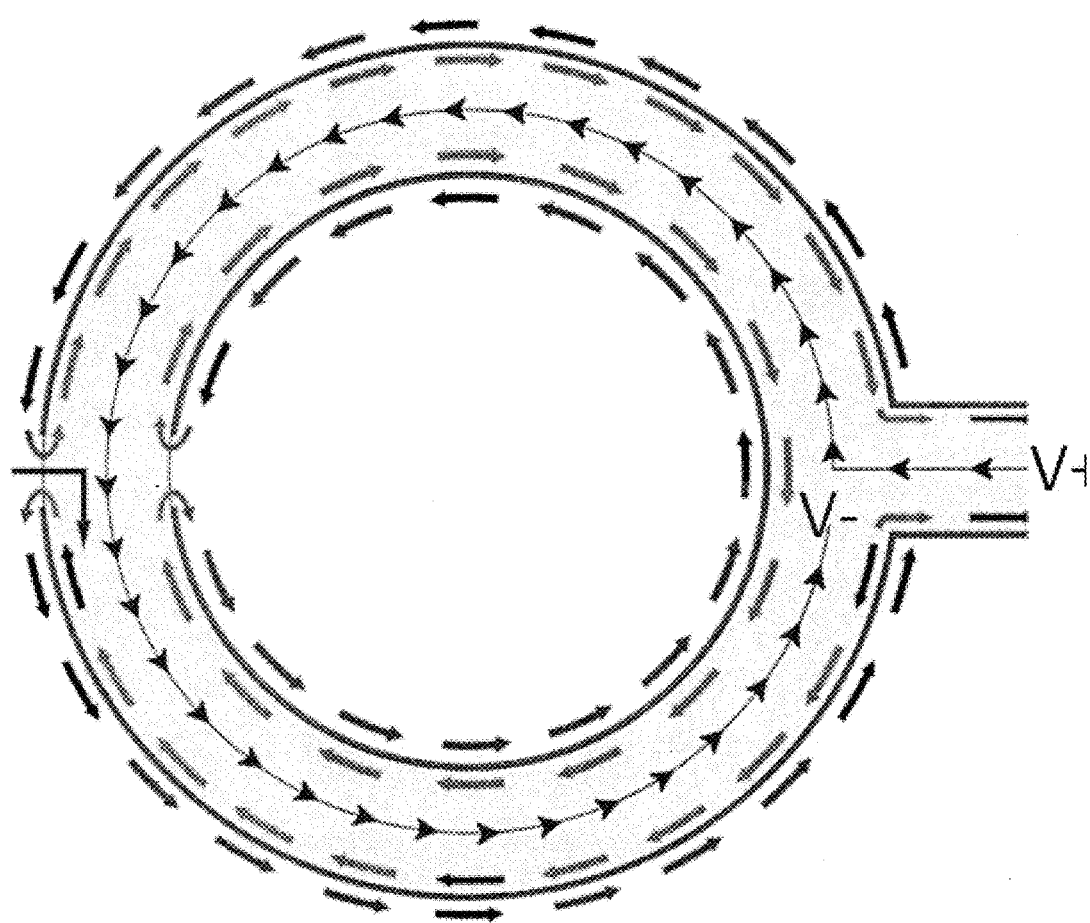
FIG. 4 is an exemplary diagram illustrating a current distribution for the exemplary coil according to an exemplary embodiment of the present disclosure.

FIG. 4 shows an exemplary diagram of the current distribution for the exemplary coil, according to an exemplary embodiment of the present disclosure. The outer conductor can include, for example, a capacitor connected with the inner conductor, which can also serve as a shield such that the coil is not radiative, which can impede transmission. The exemplary coil can also have low electromagnetic interference with the surrounding area. The potential of the two ends of the inner conductor can be equal based on the ground, which can be the potential of the shield for the outer conductor. With the capacitance formed by the inner and outer conductor resonant with the inductance of the inner conductor, the coil can be easily tuned. The outer conductor can function as a shield of the current flowing on the inner conductor. Thus, the sum of the current can be small. Additionally, the interference to the adjacent coil can be small. The exemplary coil can include a self-resonant structure, which can be routed into any shape, and can be as flexible as a transmission line connected to the coil.

FIGS. 5A and 5B show a set of diagrams of an array of traditional coils 505 (e.g., four coils with an approximately 2 mm gap between adjacent elements) and FIGS. 5D and 5E show an exemplary array of the exemplary coils 510 according to an exemplary embodiment of the present disclosure (e.g., also four coils with an approximately 2 mm gap between adjacent elements). FIGS. 5B and 5E show exemplary simulations of the H field when only one out of four coils is excited. As can be seen in FIG. 5E, only one loop array 515 is visible. FIGS. 5C and 5F illustrate coil coefficient matrices for the coils shown in FIGS. 5A and 5D, respectively. FIG. 6A shows a set of SNR maps of the exemplary array of traditional coils, which can be considered as being optimal for the traditional coils. FIG. 6B shows a set of exemplary SNR maps of the exemplary array of exemplary coils according to an exemplary embodiment of the present disclosure.

Figure 8A:
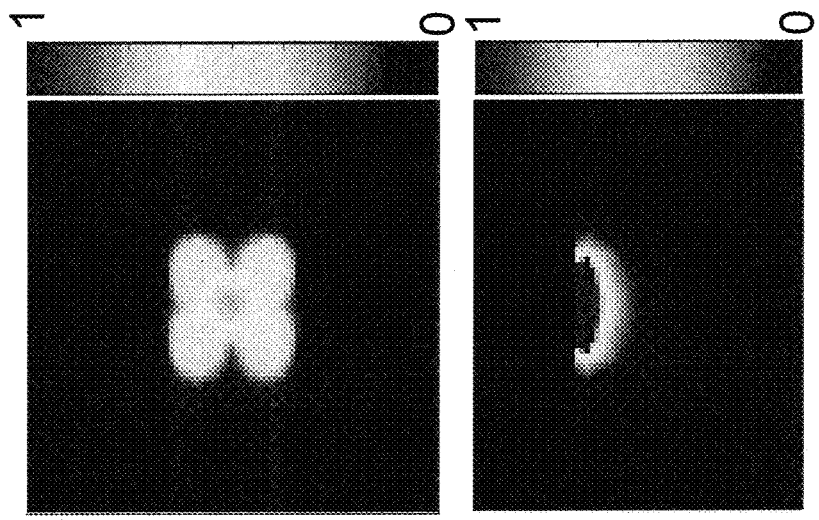
FIG. 8A is a diagram and a set of SNR maps for the further array of conventional coils.
Figure 8B:
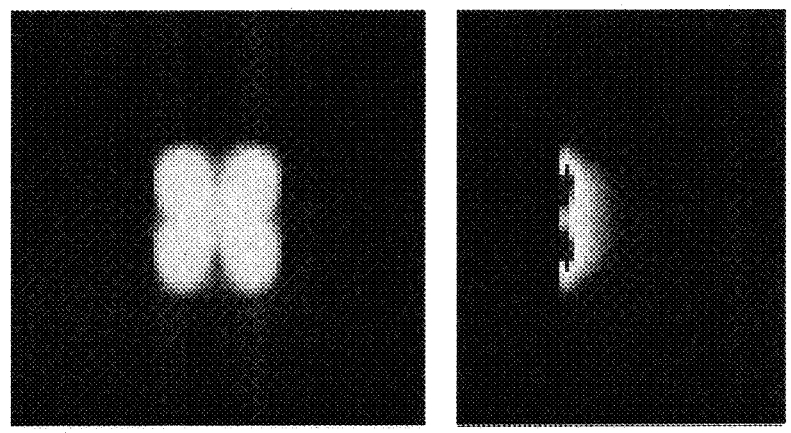
FIG. 8B is an exemplary diagram and a set of SNR maps for a further exemplary array of exemplary coils according to an exemplary embodiment of the present disclosure.

FIGS. 7A and 7B show a set of diagrams of an array of further traditional coils 705 (e.g., four coils with an approximately 2 mm gap between adjacent elements) and FIGS. 7D and 7E show an exemplary array of further exemplary coils 710 according to an exemplary embodiment of the present disclosure (e.g., also four coils with an approximately 2 mm gap between adjacent elements). As shown in FIGS. 7B and 7E, the H field can be located in the CST when excited with only one coil element. As can be seen in FIG. 7B, more than one coil 715 is visible due to decoupling. As can be seen in FIG. 7E, only one loop array 720 is visible. FIGS. 7C and 7F are coil coefficient matrices for the coils shown in FIGS. 7A and 7D, respectively. FIG. 8A shows an optimal SNR map of the further array of traditional coils. FIG. 8B shows an optimal SNR map of the further exemplary array of exemplary coils according to an exemplary embodiment of the present disclosure.

For the exemplary coil, the inductance of a solid rod can be determined by the total length of the coil, and the diameter of the inner conductor. Thus, for example:

$$L = \mu r \left[ \ln\left(\frac{8a}{bo}\right) - 1.75 \right]$$

The capacitance of the coax can be determined by the permittivity of the substrate, the diameters of the inner and outer conductors, and/or the total length of the coil. Thus, such determination can be performed using, for example, the following formula:

$$C = 2\pi \beta r / (\omega z\_0)$$

Figure 9:
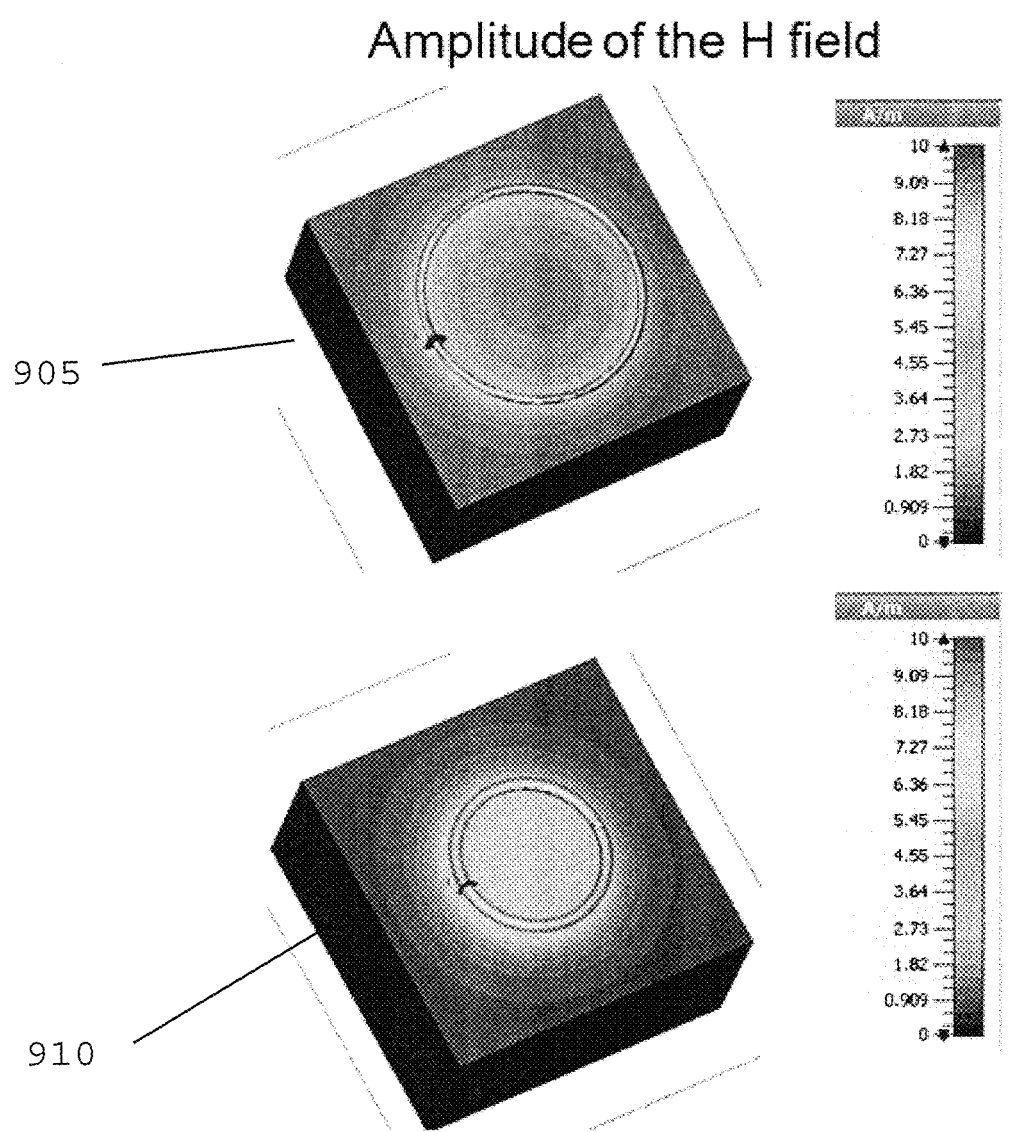
FIG. 9 is a set of exemplary diagrams illustrating an amplitude of the H field for the exemplary coil according to an exemplary embodiment of the present disclosure.
Figures 11A, 11B:
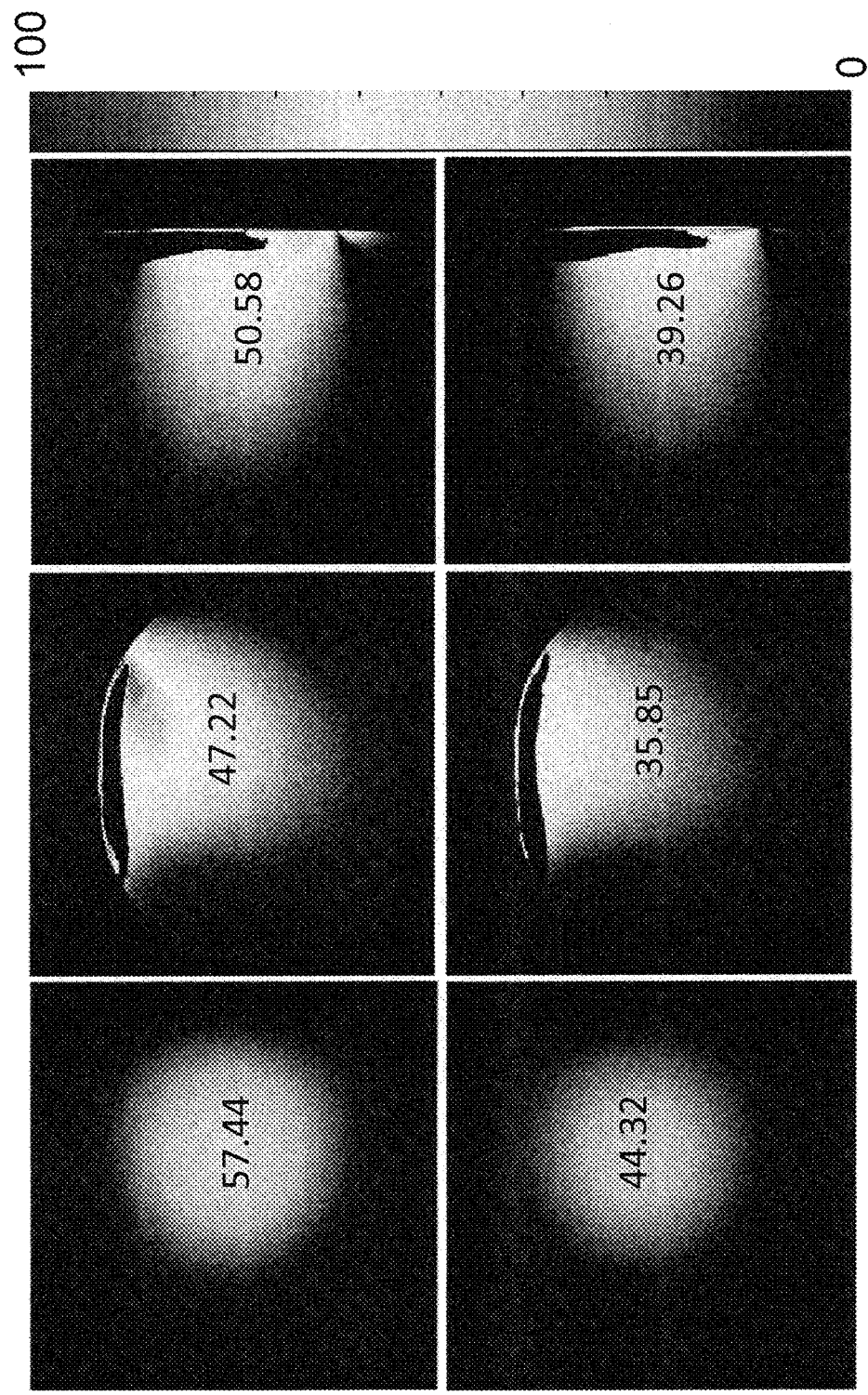
FIG. 11A is a of SNR maps for a traditional coil loop for a gel phantom.
FIG. 11B is a set of exemplary SNR maps for the exemplary coil for a gel phantom according to an exemplary embodiment of the present disclosure.

FIG. 9 shows a set of diagrams 905 and 910 illustrating the exemplary amplitude of the H field for the exemplary coil according to an exemplary embodiment of the present disclosure. FIG. 10 shows a set of graphs of the S parameter for the exemplary coil according to an exemplary embodiment of the present disclosure. The exemplary coil can include multiple modes. It can be beneficial to tune to the coil to a first mode since it can have the highest efficiency, which can be seen by the amplitude of the H field. FIG. 11A shows a set of SNR maps for a traditional coil loop and FIG. 11B shows a set of SNR maps for the exemplary coil for a gel phantom. The traditional coil has approximately 30% higher SNR than the exemplary coil.

Polycarbonate (e.g., the printing material), similar to FR4, can be sufficient to function as a substrate, but when it consists as a part of a capacitor, its loss can be too high. The amount of charge absorbed (e.g., lost) for four exemplary capacitors is illustrated below.

| Material | Charge Absorbed |
| --- | --- |
| Polystyrene | 0.05% |
| Polypropylene | 0.05% |
| Polycarbonate | 0.5% |
| Teflon | 0.1% |

For the exemplary coil, a significant SNR improvement was seen after the double sided FR4 board was replaced with Rogers4350 material (e.g., Teflon). From the exemplary impedance transformation circuit, the loss can be much lower as compared to the loss from the substrate. FIGS. 12A and 12B show a set of exemplary images of the exemplary coils and FIGS. 12C and 12D illustrate related exemplary graphs of the S21 for FIGS. 12A and 12B, respectively. FIGS. 12A-12D illustrate an exemplary double pickup coil 1205 according to an exemplary embodiment of the present disclosure.

Figure 13B:
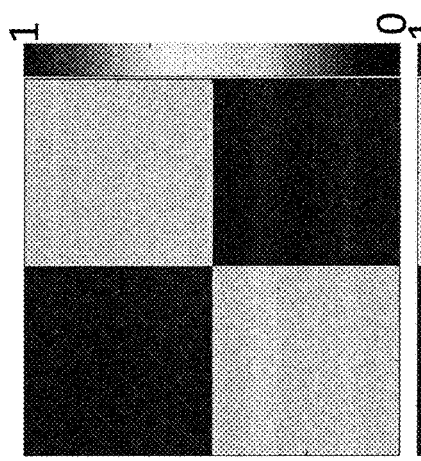
FIGS. 13A and 13B are exemplary SNR maps and a noise coefficient matrix, respectively, for the exemplary array of exemplary coils according to an exemplary embodiment of the present disclosure.
Figure 13D:
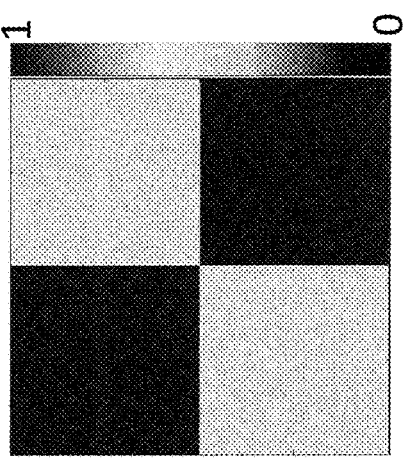
FIGS. 13C and 13D are a set of SNR maps and a noise coefficient matrix, respectively, for a traditional coil.
Figure 13A:
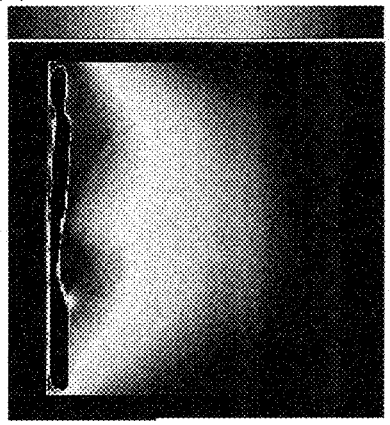
Figure 13C:
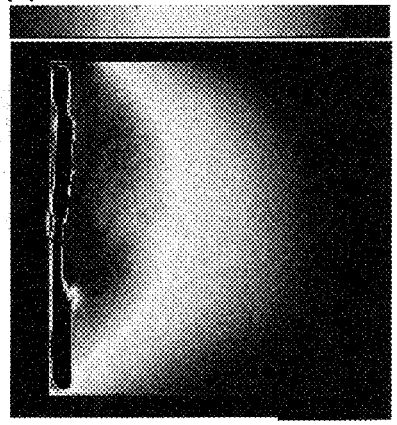
Figure 13E:
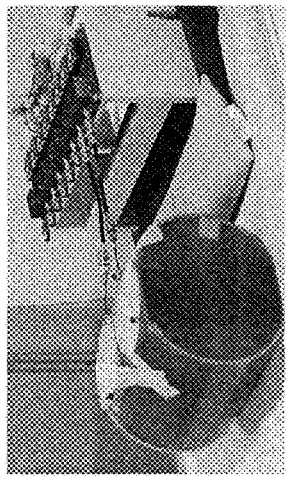
FIG. 13E is an exemplary image of the exemplary coil and a traditional coil placed side-by-side on a phantom according to an exemplary embodiment of the present disclosure.

FIGS. 13A and 13B show a set of SNR maps and a noise coefficient matrix, respectively, for the exemplary array of exemplary coils according to an exemplary embodiment of the present disclosure. FIGS. 13C and 13D illustrate a set of SNR maps and a noise coefficient matrix, respectively, for a traditional coil. Two coils can be placed side by side on a phantom. (See e.g., image shown in FIG. 13E). Because the coils can be sufficiently large, and the coupling between the coils can be damped by the load, there may not be a significant coupling issue in this exemplary scenario.

FIGS. 14A and 14B show a further set of SNR maps and a noise coefficient matrix, respectively, for the exemplary array of exemplary coils according to an exemplary embodiment of the present disclosure. FIGS. 14C and 14D illustrate a set of further SNR maps and a noise coefficient matrix, respectively, for a traditional coil. Two coils can be placed side by side on a phantom lifted up by about 1.5 cm. (See e.g., FIG. 14E). Because the coils are away from the phantom, the coupling can be strong, which may cause a coupling issue.

Figure 15:
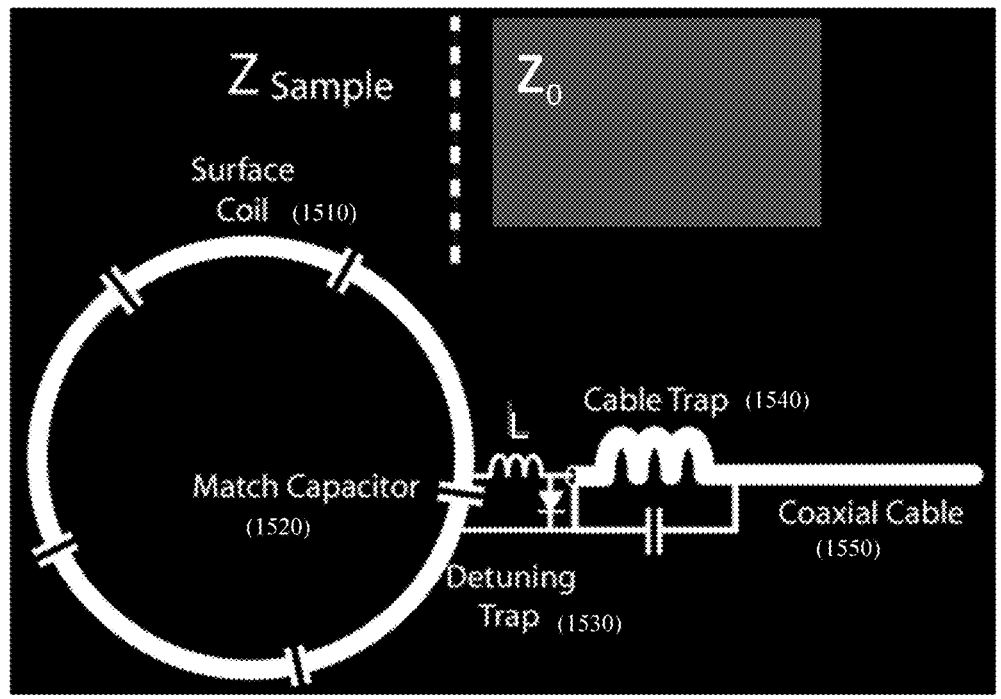
FIGS. 15-17 are exemplary diagrams of the exemplary coil according to various exemplary embodiments of the present disclosure.
Figure 16:
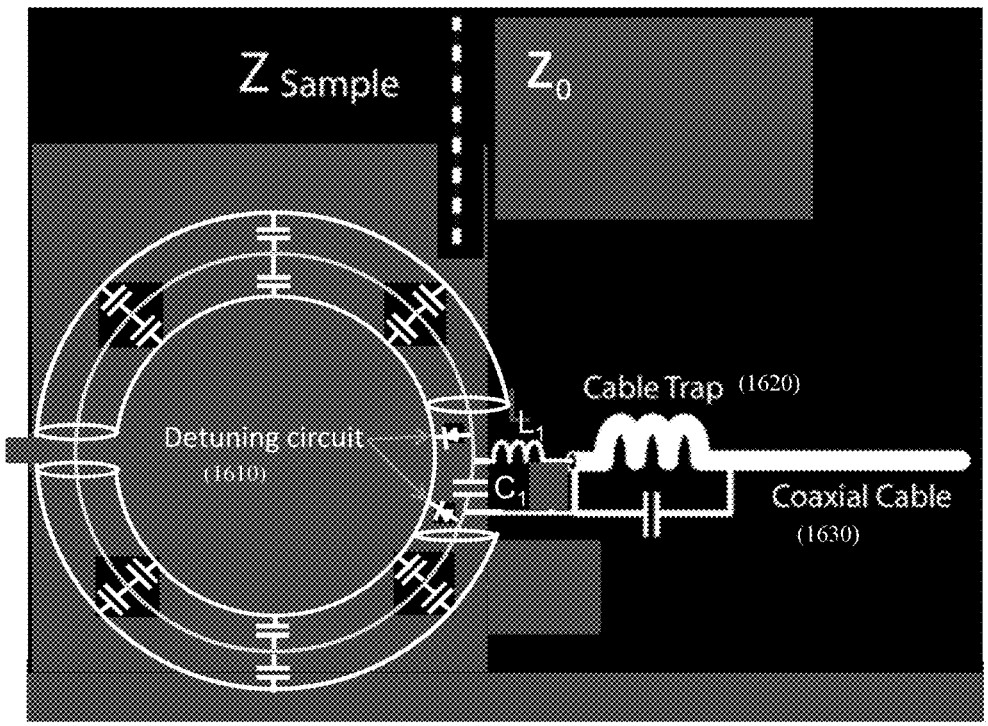
Figure 17:
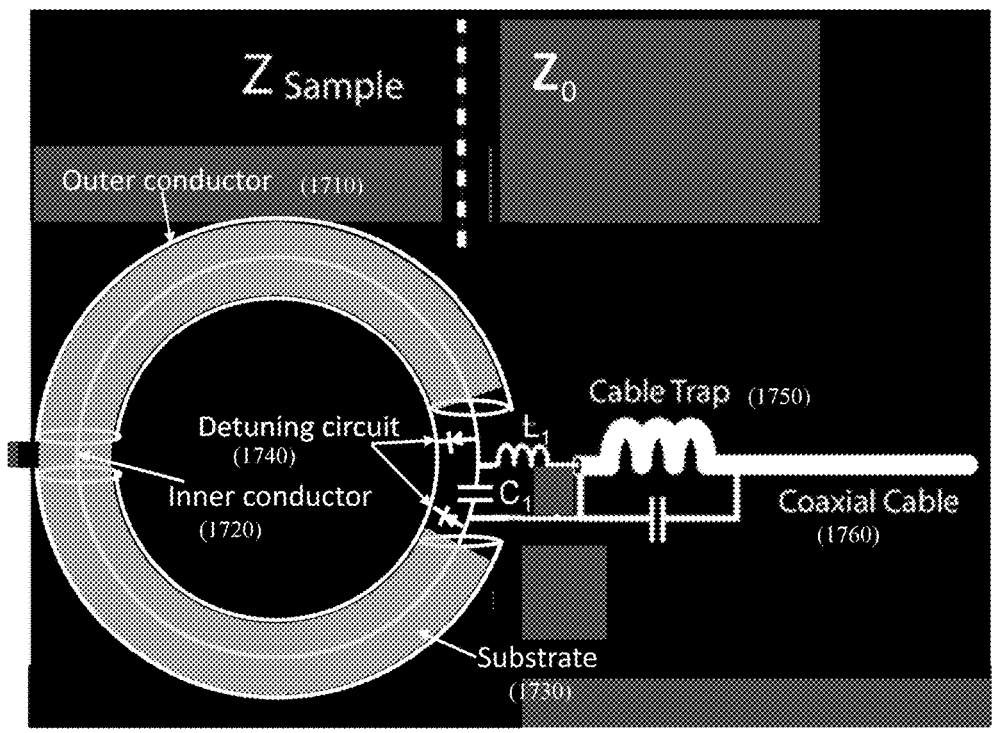

FIGS. 15-17 show exemplary diagrams of the exemplary coil according to an exemplary embodiment of the present disclosure. The inductor L can be chosen to be resonant with a matched capacitor at the magnetic resonance ("MR") frequency where the diode can be forward biased.

FIG. 15 shows an exemplary surface coil 1510, match capacitor 1520, detuning trap 1530, cable trap 1540, and coaxial cable 1550. FIG. 16 shows exemplary detuning circuit 1610, cable trap 1620 and coaxial cable 1630. FIG. 17 shows exemplary outer conductor 1710, inner conductor 1720, substrate 1730, detuning circuit 1740, cable trap 1750 and coaxial cable 1760.

Many, if not all, traditional coil designs are formed and constrained by the fundamental properties of the building blocks of the receive coil element itself (e.g., based on the fact that traditional low impedance coils interact with one another). However, the exemplary high impendence coils do not interact with one another. Thus, they can be placed freely on any desired shape. Moreover, the exemplary coils do not have to maintain a fixed relation/distance/overlap between the coils them. Therefore, the exemplary coils can be formed into various suitable shapes. For example, the exemplary coil arrangement can be fit on to a hat, which can provide a near perfect fit for each subject. Further, the exemplary coil arrangement does not need rigid lumped elements. Traditional lumped elements can be similar to solid bricks. In contrast, the exemplary coil arrangement can be made flexible. Thus, the exemplary coil arrangement can be integrated into a blanket, which can be wrapped around any subject (e.g., a baby), or for complicated cases such as a fractured arm which may not fit into a traditional coil.

Further, the exemplary coil arrangement can be used in an exemplary fast imaging procedure to image moving joints to see how the nerves, tendons, muscles, and cartilage behave under stress, or at different points in a motion cycle. The exemplary coil arrangement can be detuned at all frequencies at once. This can make the exemplary coil suitable for multi nuclear coil designs, which operate at multiple frequencies. The exemplary coil arrangement can also be easier to produce.

The exemplary coil arrangement can be used with in any anatomical structure. For example, a flexible blanket coil can be used for pediatric patients, an elastic cap coil can be used that can fit different sizes of heads, and a wideband coil array can be used in multi-nuclear imaging.

The exemplary coil arrangement according to an exemplary embodiment of the present disclosure can include, for example (i) a continuous inner conductive path, (ii) a substrate and (iii) an outer conductive path segmented into two symmetrical pieces. The exemplary substrate separating the inner and outer conductive path can form a distributed capacitor, which can result in a very high impedance circuit. (See e.g., coil shown in FIG. 2). In this exemplary configuration, the net sum of current flowing in the inner conductive path and outer conductive path can approach zero. Thus, the electromagnetic interference to its adjacent coil elements can be neglected. Moreover, in contrast to conventional receive coil elements, the exemplary coil arrangement can function at a range of frequencies provided that the sum of current on the coil can remain small enough. The exemplary coil arrangement can be any shape, and the inner conductor can be off center relative to the outer conductor, as long as the composite structure can create a very high impedance with the inductance of the inner conductor.

The received signal can be received from the exemplary coil arrangement in different exemplary manners. For example, the potential between the two ends of the inner conductor can be measured, while the outer conductor can be connected to the RF ground plane. Alternatively, or in addition, the potential between the two ends of the inner conductor can be measured, while the outer conductor can be floating.

To deactivate the exemplary coil arrangement during transmit, any suitable mechanism can be used that can alter the impendence of the coil. This can include, but is not limited to, using PIN diodes connecting the inner and outer conductor at each side. For example, the two PN diodes can be activated to connect the inner and outer conductors, such that no capacitance can be formed between them. This detuning circuit can function more efficiently than those detuning circuits found in the conventional coils since it can detune the coil at all frequencies. Conventional coils are generally only detuned at a single frequency.

When the received signal can be picked up from the two ends of the inner conductor, there can be a LC matching circuit connected to the two ends of the inner conductor to match the impedance of the coil to the noise matching impedance of the preamp. (See e.g., coil shown in FIG. 2). The received signal can also be acquired by measuring the potential between the inner conductor and the outer conductor at one end, while the outer conductor can be connected to the RF ground plane, as long as the symmetry of the structure at both ends can remain, and no extra reactance can be introduced between the two ends of the inner conductor or between the inner conductor and outer conductor from the viewpoint of the coil.

The exemplary substrate can provide a superior quality factor to provide a low loss capacitance with the inner conductor and outer conductor. There can be an insulating layer outside the outer conductor to separate the coil elements, and to prevent direct contact with the subject.

Exemplary High-Impedance NMR Detector

A function of inductive detectors can be to measure the electromotive force ("EMF") induced by the NMR signal.

Traditional low impedance coils ("LIC") efficiently capture the EMF, but can also facilitate current to flow. This current, in turn, can create a secondary RF field that can be detected by neighboring elements. To eliminate resonant inductive coupling between elements, an exemplary coil design can be used, which can facilitate the EMF to be measured without facilitating current to flow and signal to leak inductively into neighboring elements.

As shown in FIG. 18B, the exemplary apparatus can include a high impedance resonant coaxial NMR probe. (See e.g., Reference 16). In contrast to conventional LIC elements, there may not be any lumped capacitors to adjust the resonance frequency or distribute the current. Instead, the exemplary HICs were tuned by adjusting the length, the relative permittivity of the substrate, and the ratio between inner and outer conductor diameter (See e.g., Reference 17), such that the Larmor frequency of interest can coincide with the lowest resonance of the structure. EM simulations (e.g., CST microwave studio, Darmstadt, Germany) show that the current on the inner conductor increases approximately linearly from zero at the gap to a maximum at the gap of the outer conductor, which can be mirrored by an opposing current distribution on the inner surface of the outer conductor. As shown in FIGS. 23A-23F, at the gap in the outer conductor, skin depth effects can facilitate a current to flow through the gap onto the outer surface of the conductive wrapping of the coil, and this current can travel uniformly towards the other edge of the gap. Shorting the gap in the inner conductor through the outer conductor can preclude the formation of the appropriate mirror currents, eliminating all resonances across a broad spectrum (See, e.g., FIG. 18C), which can facilitate the coil to be detuned with PIN diodes during excitation. FIG. 23F shows a graph illustrating the average surface current density for the exemplary inner conductor 2305, the exemplary inner surface of the outer conductor 2310, and the exemplary outer surface of the outer conductor 2310 according to an exemplary embodiment of the present disclosure.

This can also be used to suppress the current induced by the NMR phenomenon during signal reception. This suppression of currents can represent a fundamental difference between LICs 1820 and HICs 1815. (See, e.g., FIG. 18D). To suppress the induced current, LIC elements utilize high impedance at the port, whereas a low impedance across the port can be utilized in HIC elements. Consequently, implementing a "reverse preamplifier decoupling" can create a low impedance at the port, can suppress all currents in a HIC arrangement, provided that the impedance at the port can be significantly lower than the intrinsic impedance of the HIC itself (approximately 2 kΩ). Whereas creating a sufficiently low impedance at the LIC port can be possible only at one isolated frequency, and utilizes precise fine tuning of the preamplifier interface, reversed preamplifier decoupling in a HIC arrangement can suppress all currents over a wide range of conditions.

Figure 24:
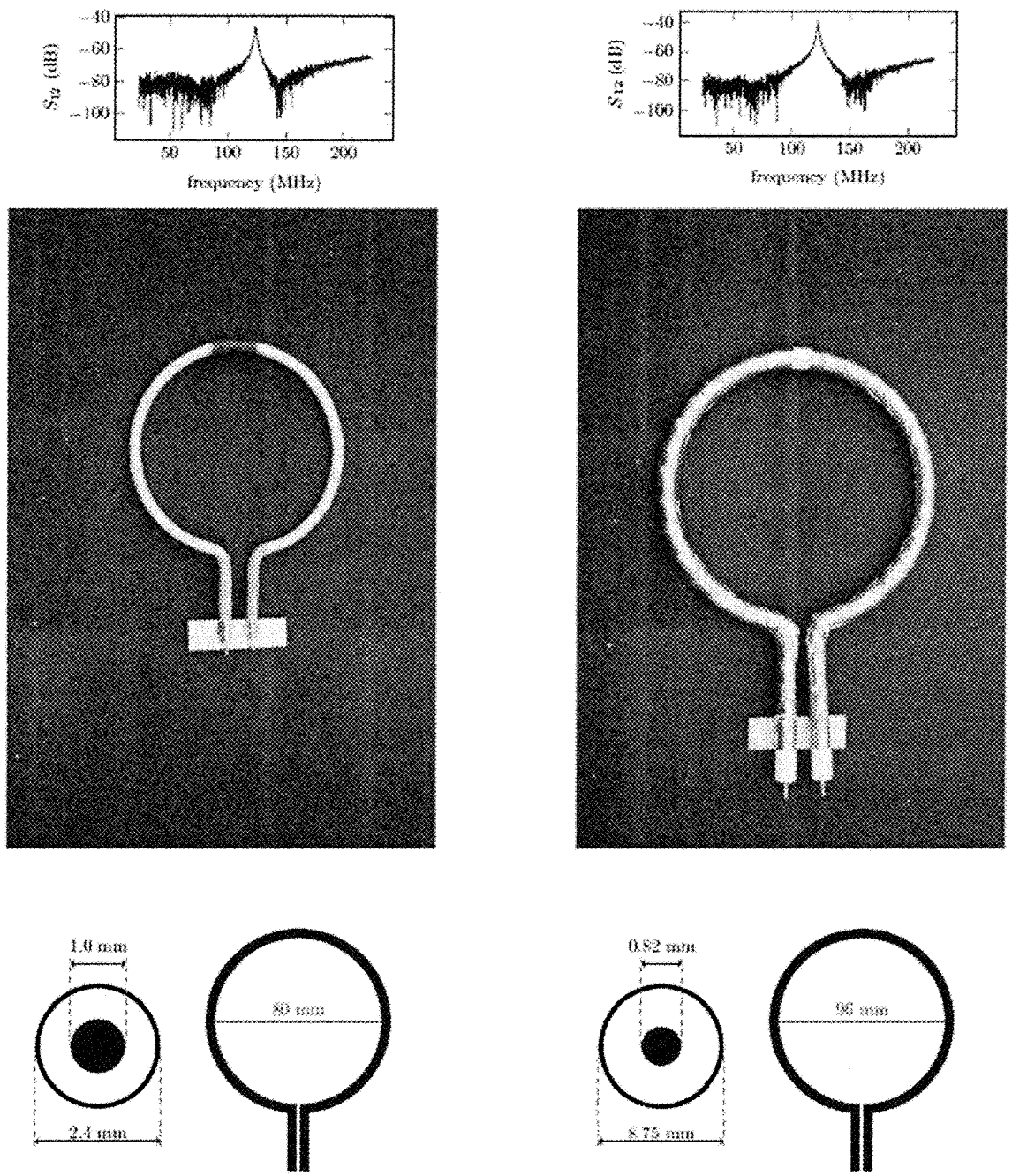
FIG. 24 is a set of frequency graphs, coil images and coil diagrams comparing two 3D printed HIC elements resonating at the same frequency according to an exemplary embodiment of the present disclosure.
Figures 25A, 25B:
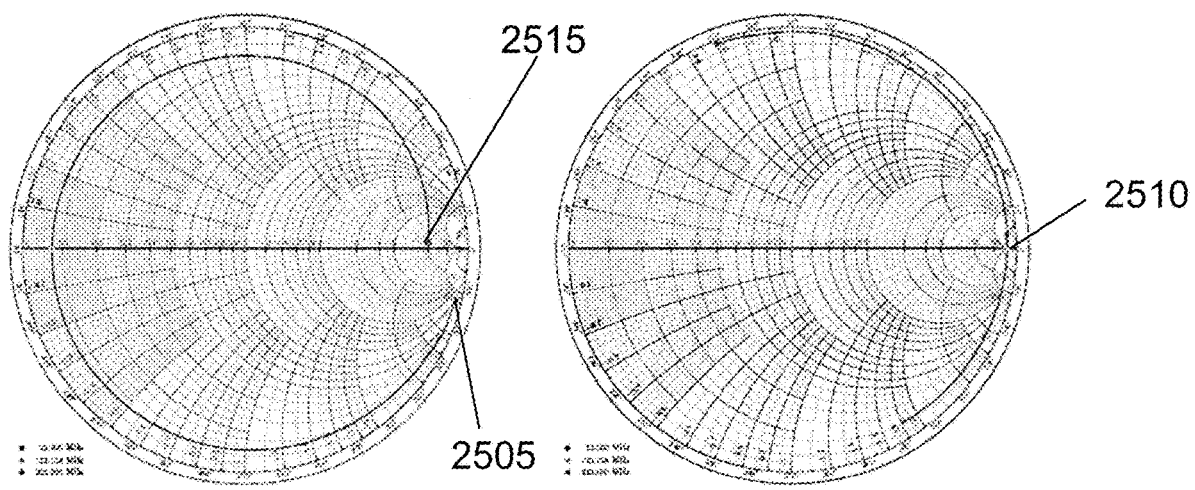
FIG. 25A is an exemplary Smith chart for the low impedance coil according to an exemplary embodiment of the present disclosure.
FIG. 25B is an exemplary Smith chart for the high impedance coil according to an exemplary embodiment of the present disclosure.

A 3D printer (e.g., Fortus 360mc, Stratasys, Minn.) was used to explore the design space of coaxial substrate configurations. (See, e.g., FIG. 24). The lack of lumped elements (See e.g., Reference 18-23) in combination with the coaxial design (See e.g., Reference 24) can suggest that a high degree of mechanical flexibility can be possible with the exemplary HIC coils. Given the possibility to make a more flexible coil in addition to leveraging the desirable decoupling properties of HICs, a 0.7 mm separation between the inner and outer conductor was used, with the effective resolution limit of the exemplary printer for this type of structure, which lead to a coil diameter of about 8.0 cm when tuned to about 123 MHz, the proton Larmor frequency of the exemplary 3 Tesla MRI scanner (Siemens, Erlangen, Germany). In addition to the data shown in the graph of FIG. 18D, the high-impedance nature of the exemplary HIC elements can also be seen in the Smith charts showing S1,1 vs. frequency for 23.000 MHZ (e.g., element 2505), 123.158 MHz (e.g., element 2510) and 223.000 MHz (e.g., element 2515). (See, e.g., FIG. 25).

High- Vs. Low-Impedance Detectors

To evaluate how well HICs cloak themselves from one another, three identical HIC elements were placed side by side on top of a large conductive phantom. (See, e.g., coils shown in FIG. 19A). MR images were obtained with each coil individually (See e.g., FIG. 19B), and also with all coils active simultaneously. (See, e.g., FIG. 19C). For comparison, three conventional 8-cm-diameter LICs were constructed (See e.g., FIG. 19D) and used for imaging under identical circumstances. When all coils were active at the same time, the signals measured using LICs were distorted due to coupling (See, e.g., comparison of FIGS. 19E and 19F), whereas the receive profiles of the HICs remain unaltered. (See e.g., comparison of FIGS. 19B and 19C.

Figures 20A, 20B:
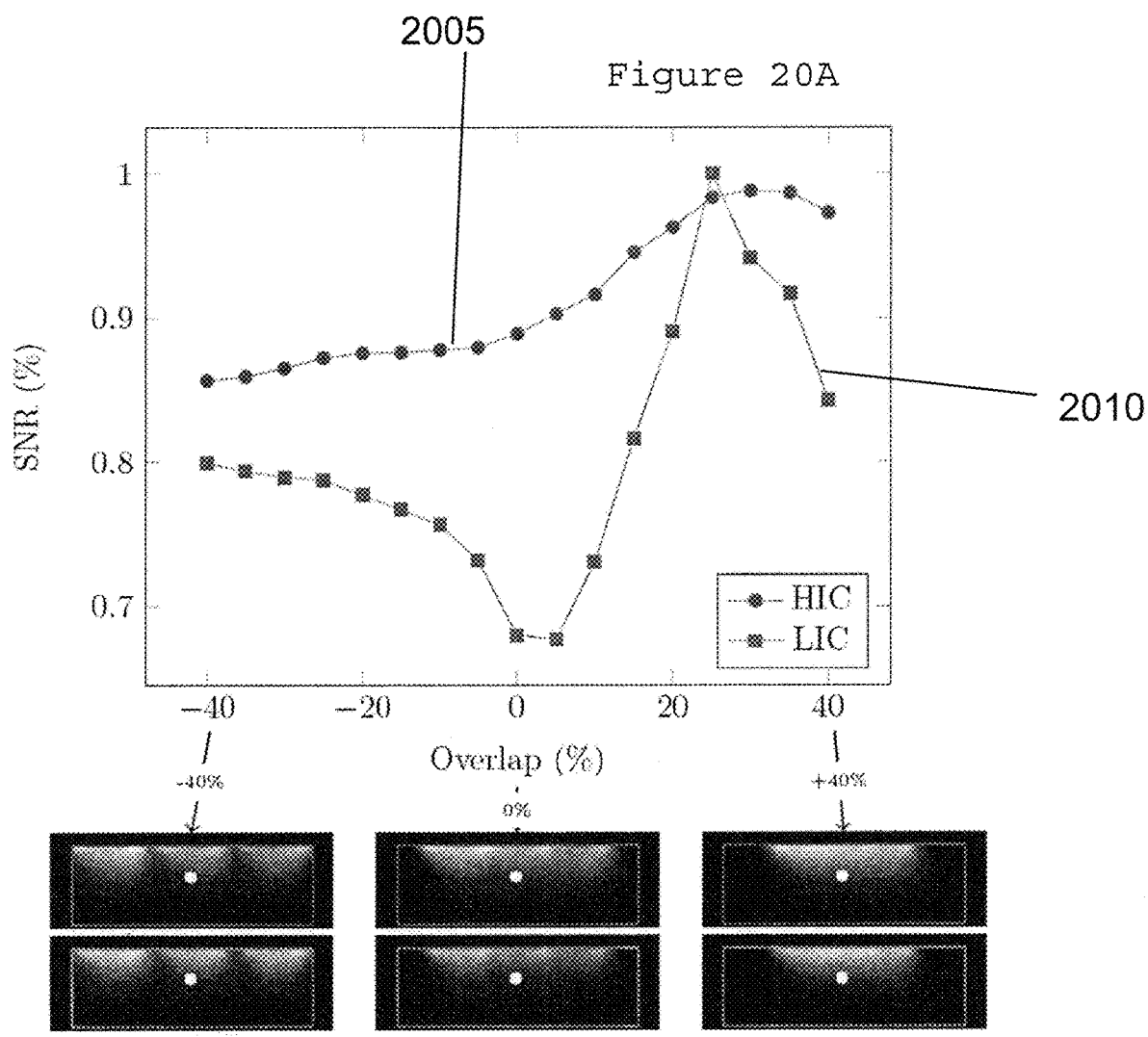
FIG. 20A is an exemplary graph of SNR degradation due to coupling between neighboring coil elements as a function of coil overlap according to an exemplary embodiment of the present disclosure.
FIG. 20B is a set of exemplary images showing combined signal images according to an exemplary embodiment of the present disclosure.

Although distinct coil-profiles can be a feature of the NMR phased array, crucial for parallel imaging (See, e.g., References 25-27) and modern multi-band techniques (See, e.g., References 28 and 29), decoupling should not come at the expense of a reduced signal to noise ratio ("SNR"). In order to determine this, the SNR was evaluated at a 4.2 cm (e.g., approximately ½ the coil diameter) depth below the center element as a function of coil overlap. (See, e.g., FIG. 20A). LIC elements 2010 can reach their optimal performance when critically overlapped (approximately 25% of the diameter). When the outer coil elements can be moved further apart or closer together, the SNR can quickly deteriorate. The HIC 2005 elements, conversely, show almost no degradation in SNR as the overlap between them can be changed. A similar analysis performed on a cylindrical surface is shown in FIGS. 21A-21C.

Exemplary High-Impedance Detector-Array Glove

To illustrate the various degrees of freedom provided by the exemplary HIC elements, an exemplary wearable coil in the form of a glove was created. (See, e.g., FIGS. 21A-21C). Eight HIC elements were stitched onto a cotton glove. The contours of each finger can be traced by an individual coil, facilitating all the joints in each finger to articulate freely. Two additional elements were stitched on the top of the hand and wrist, and one additional element was stitched on the bottom, facilitating the carpal bones in the wrist joint to be studied as well.

Figure 21A:
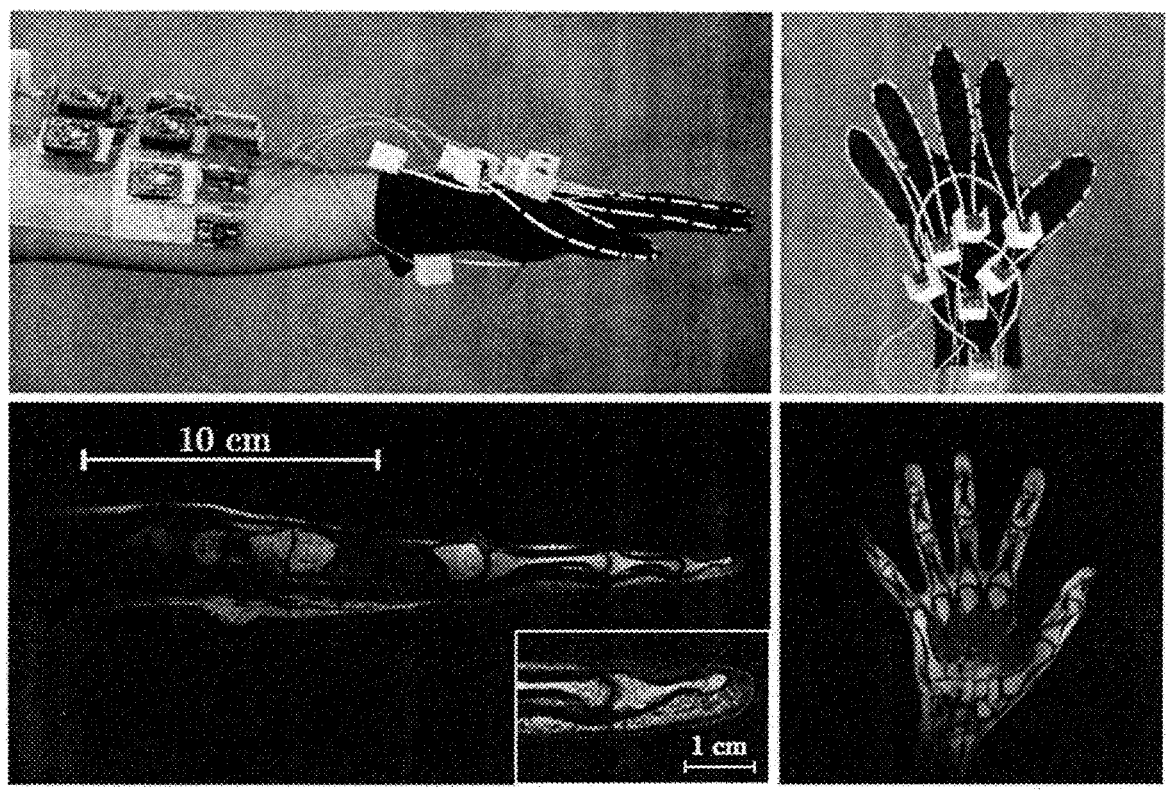
FIG. 21A is an exemplary image of a glove coil with the hand starched out and corresponding T1 weighted MR images generated using the glove coil according to an exemplary embodiment of the present disclosure.
Figure 21B:
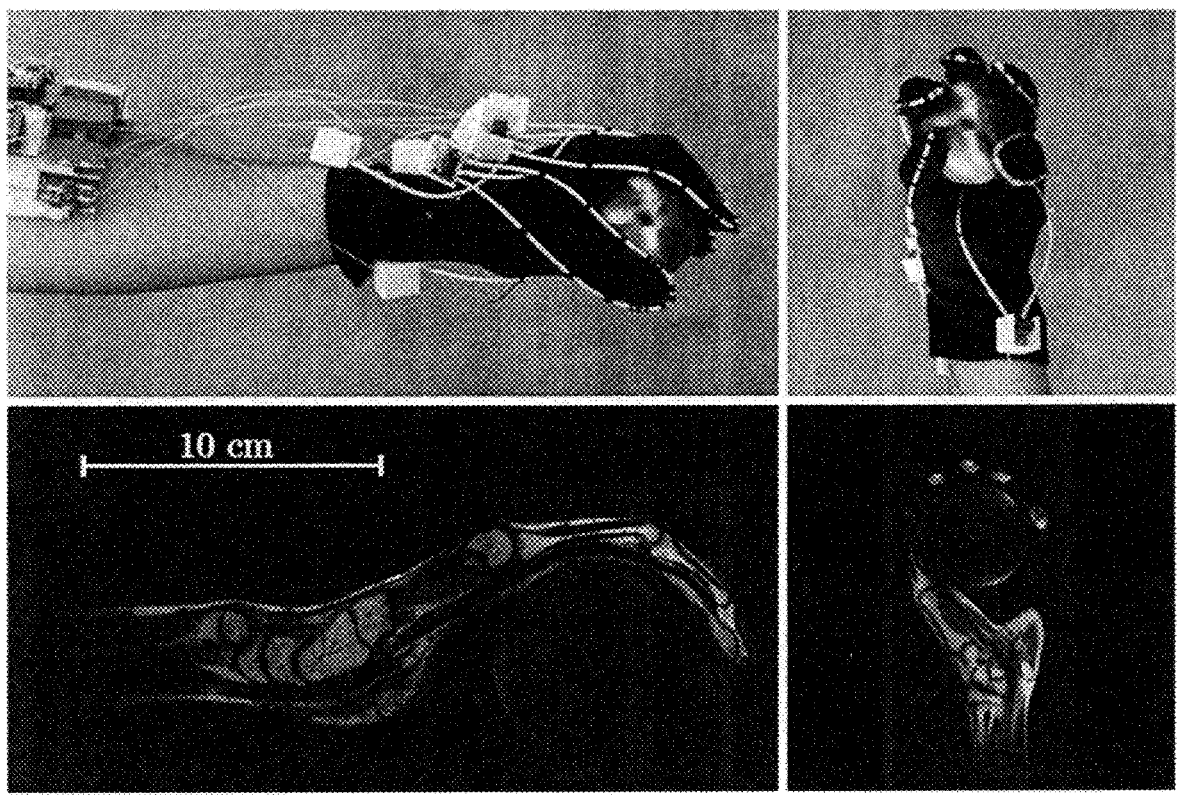
FIG. 21B is an exemplary image of a glove coil holding a peach and corresponding T1 weighted MR images generated using the glove coil according to an exemplary embodiment of the present disclosure.
Figure 21C:
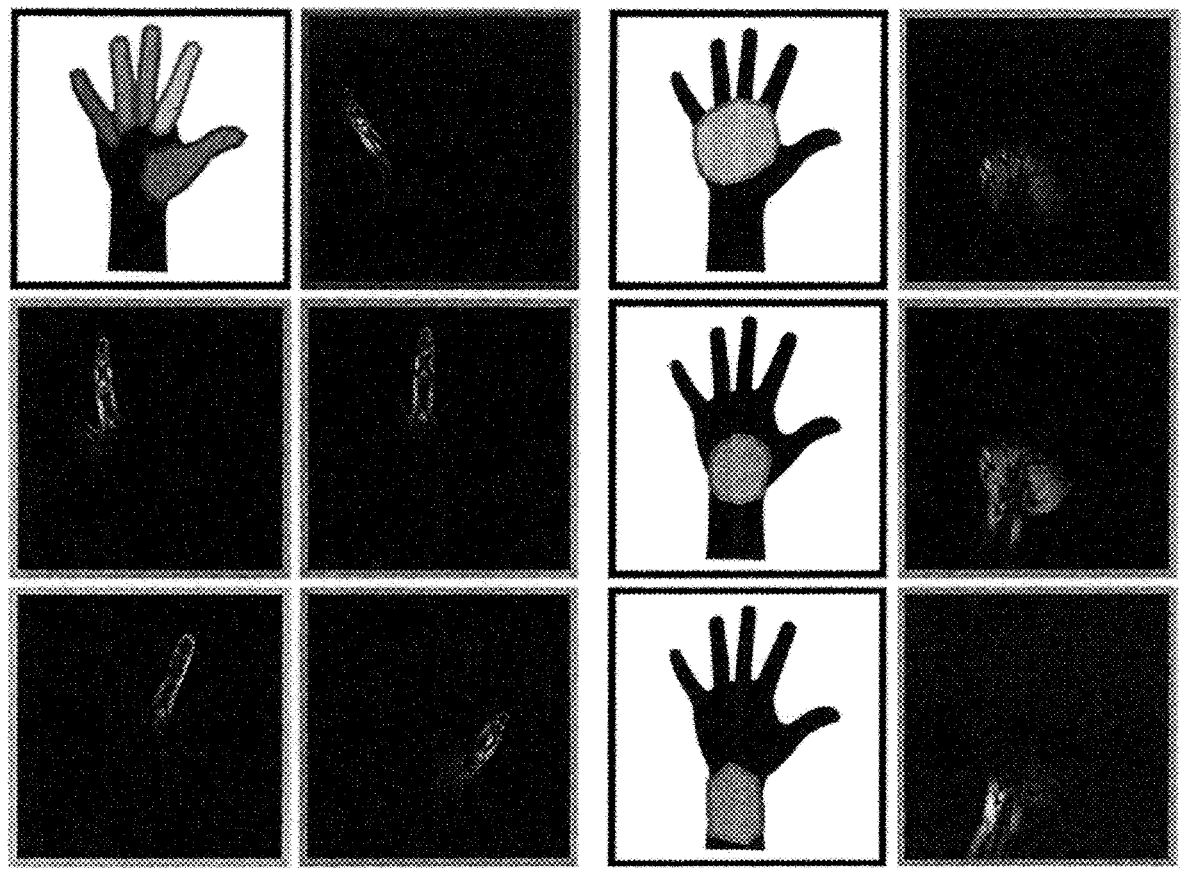
FIG. 21C is a set of exemplary illustrations showing where the individual coil elements are located on the hand next to the individual coil images obtained during a single T1 weighted measurement with all coils simultaneously activated according to an exemplary embodiment of the present disclosure.
Figure 27:
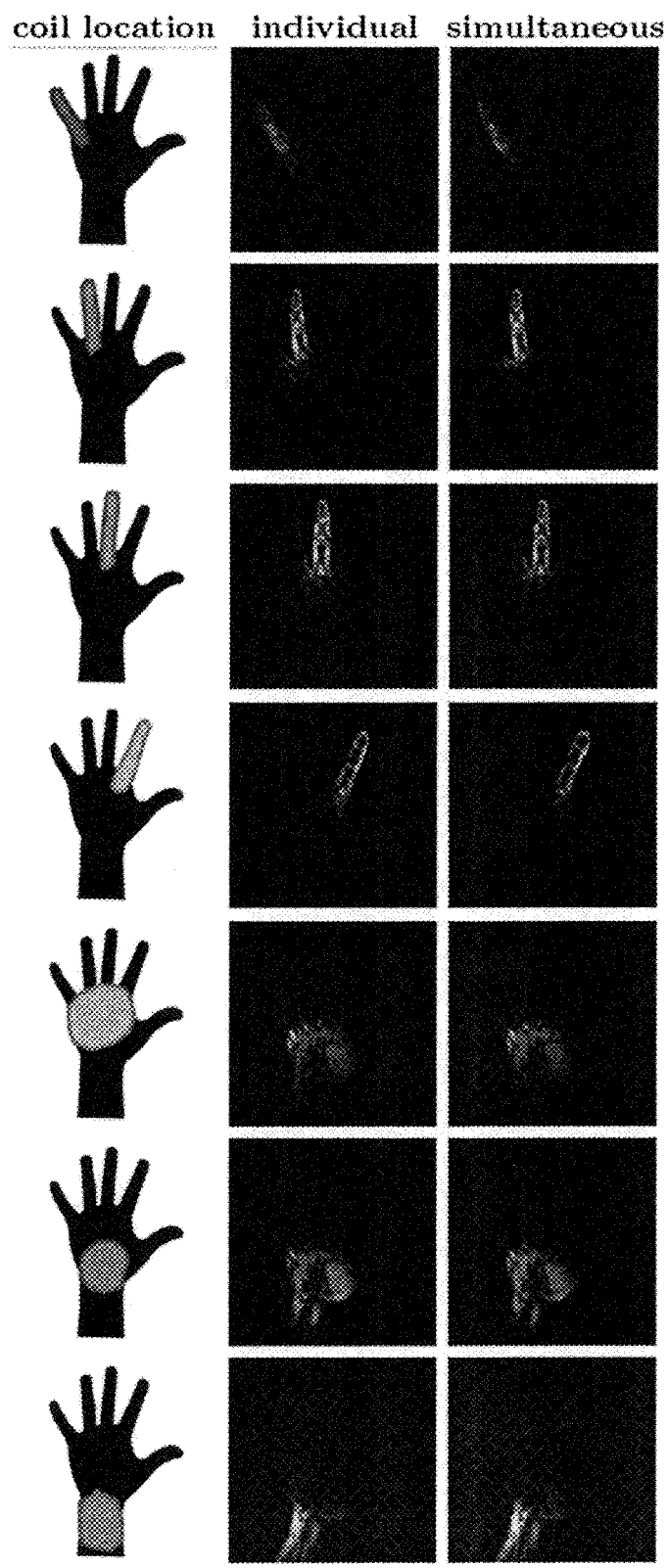
FIG. 27 is a set of coil locations and associated generated images according to an exemplary embodiment of the present disclosure.
Figure 28:
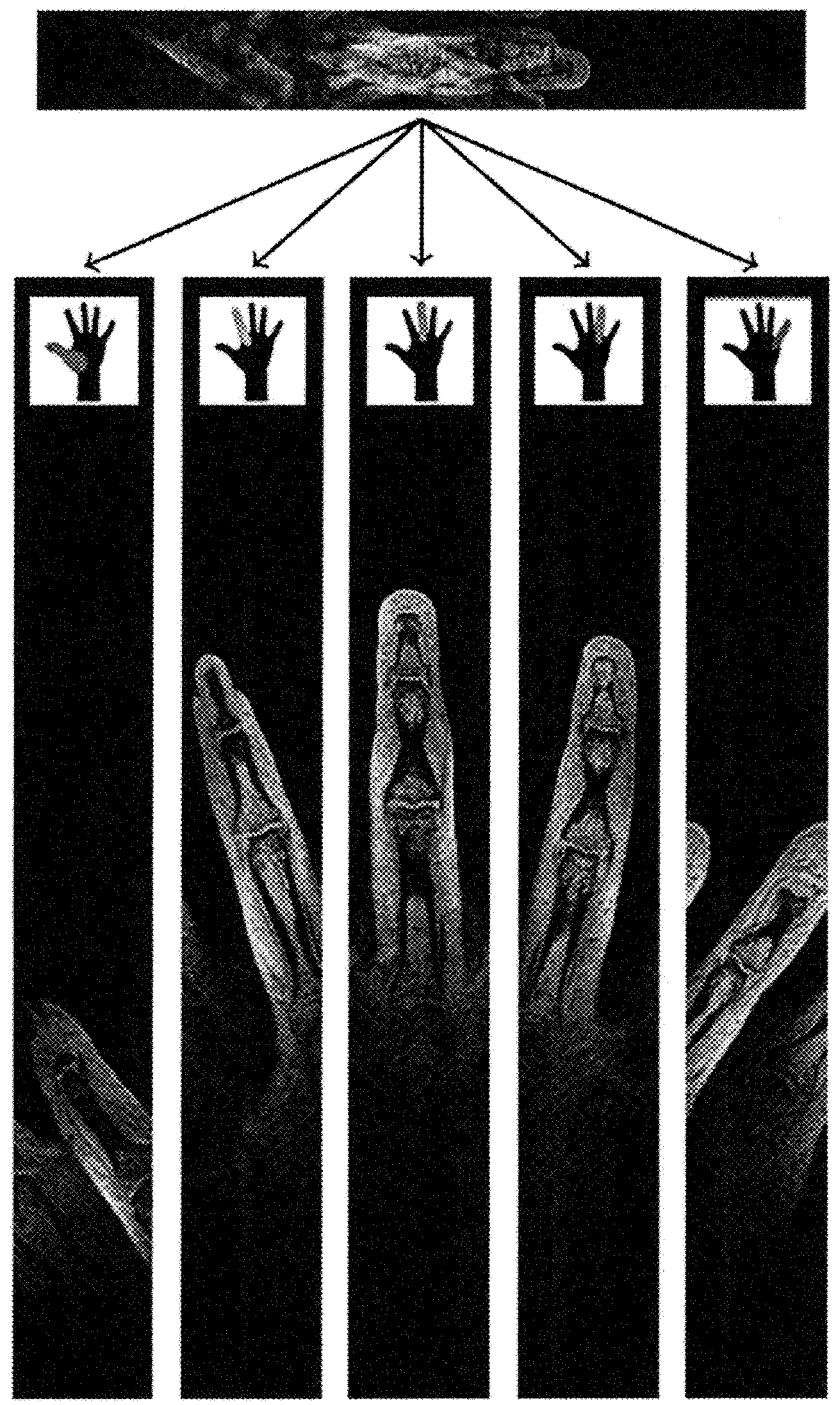
FIG. 28 is a generated three-dimensional data set acquired covering only the middle finger according to an exemplary embodiment of the present disclosure.

FIG. 21A shows a coronal and sagittal slice through the hand, stretched out flat on top of the patient table. The close-fitting elements enable fast imaging with precise detail (about 250 µm, 2 mm slice). Although the coil elements on each finger can be directly adjacent to one another in this configuration, distinct coil profiles can be maintained. (See e.g., FIGS. 21C and 27). Another exemplary feature of the exemplary glove array, where each individual element traces a distinct anatomical feature, can be the ability to isolate individual fingers simply by selecting the appropriate coil. Alternatively, a factor of 5 in acceleration can be achieved without g-factor penalty (See e.g., Reference 26), by facilitating all fingers to alias on top of one another, and relying purely on the coil signal isolation to directly reconstruct the individual images belonging to each finger. (See e.g., FIG. 28).

The flexibility of the exemplary HIC elements, combined with their immunity from electrodynamic coupling, can facilitate the visualization of the intricate dynamics between ligaments, tendons and muscles during complex motions such playing piano/typing or grasping objects. Thus, exemplary HIC elements open up new avenues for the study of complex joint motion, facilitating, for example, the diagnosis, monitoring, and treatment of repetitive strain injuries in athletes, musicians, and others.

Figure 29:
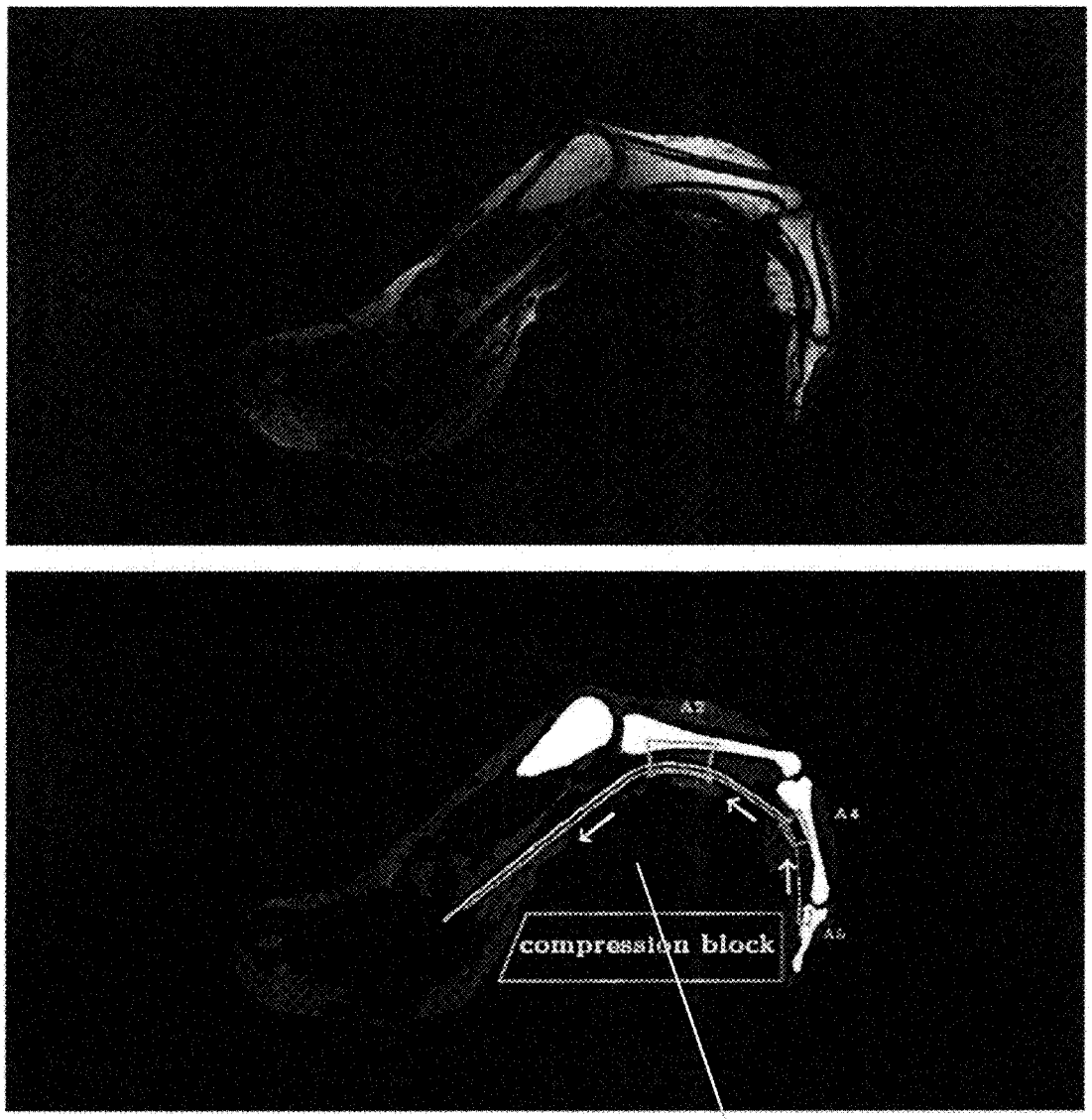
FIG. 29 is a set of sagittal T1 weighted image through the flexor tendon in the index finger while squeezing a block of wood according to an exemplary embodiment of the present disclosure.
Figure 30:
FIG. 30 is an exemplary sagittal T1 weighted image through the flexor tendon in the index finger while the hand is stretched out according to an exemplary embodiment of the present disclosure.
Figure 31:
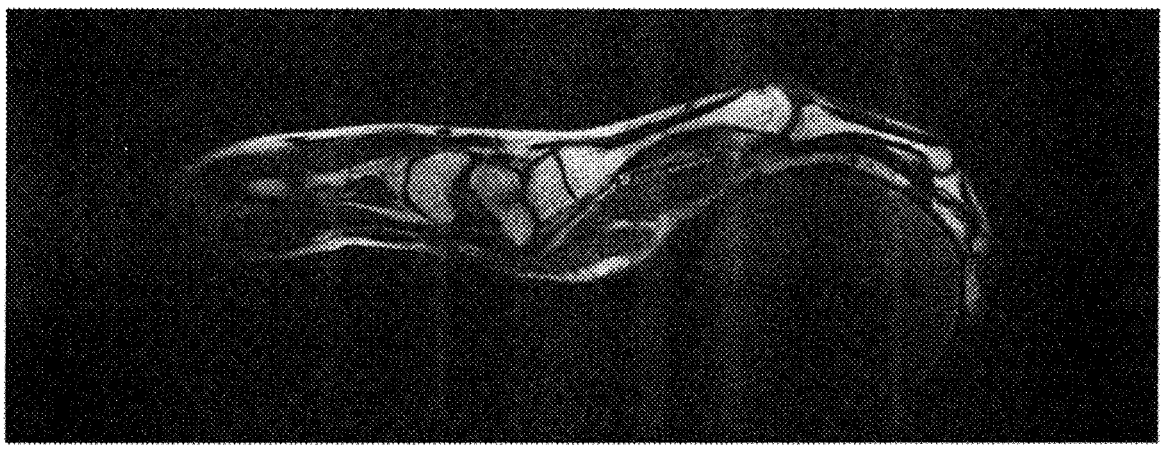
FIG. 31 is an exemplary sagittal T1 weighted image through the flexor tendon in the index finger while the hand is holding a peach according to an exemplary embodiment of the present disclosure.

FIG. 21B shows the same hand in a different position, now holding a peach, to illustrate how the HIC elements conform to the shape of the hand. Because of the robustness to variations in coil overlap, the performance of the close-fitting coils remains unperturbed, facilitating the study of intricate structures such as the pulley and flexor arrangement in different positions, and even under load. (See, e.g., FIG. 29). Although pulley ligaments and flexor tendon can almost be indistinguishable based on underlying contrast (e.g., both have short T2 relaxation times), their interaction can now be examined by squeezing an object 2905 during the scan (See e.g., FIG. 29), revealing how the pulley arrangement guides the flexor tendons and distributes the load. (See e.g., FIGS. 30 and 31).

Figure 32:
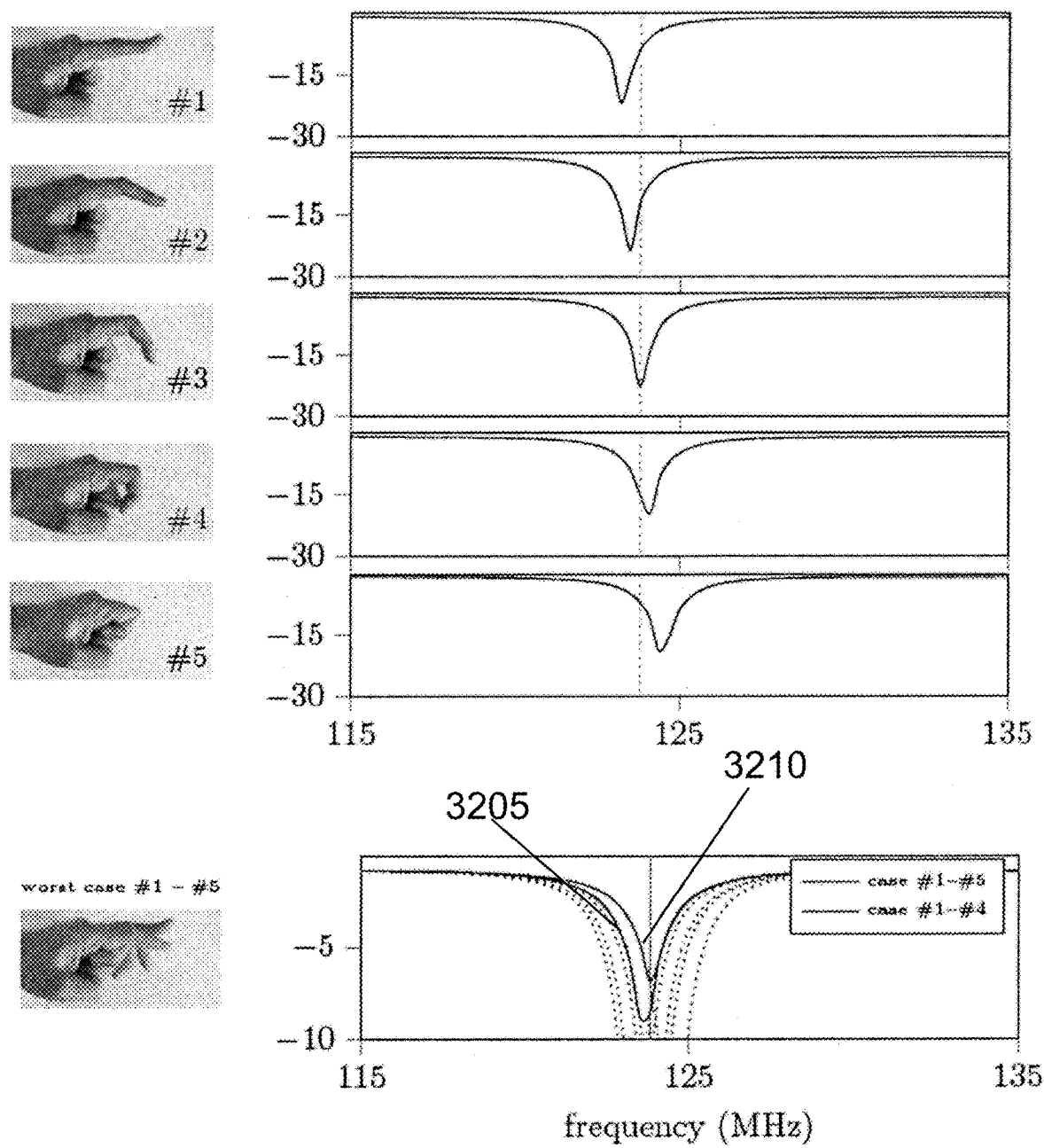
FIG. 32 is a set of images of a hand and corresponding graphs illustrating the $S_{1,1}$ according to an exemplary embodiment of the present disclosure.

Although the exemplary HIC design can be extremely flexible and nearly immune to coupling effects, the inductance of the coil can still be influenced by bending. (See e.g., elements 3205 and 3210 shown in FIG. 32). However, the extremely close fit of the glove coil, made possible in part by its flexibility and adjustability, creates a heavy loading condition, which helps to suppress these effects, thus facilitating for a large range of motion.

Figure 22:
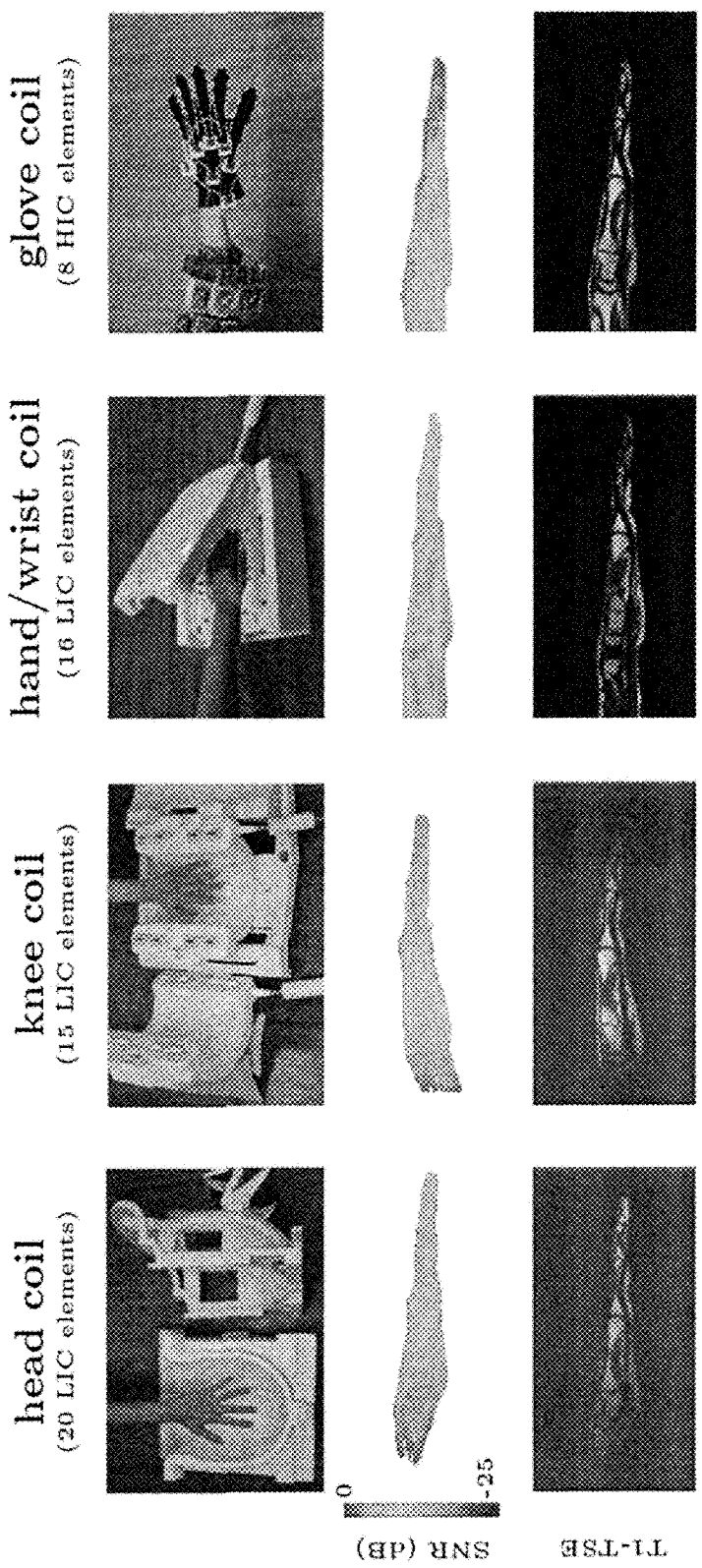
FIG. 22 is a set of images of various configurations of a LIC coil compared to the exemplary HIC glove coil, and corresponding SNR maps and generated images according to an exemplary embodiment of the present disclosure.

In order to evaluate the results, an in vivo evaluation of the SNR and flexibility provided by the glove coil was compared to three state-of-the-art LIC phased arrays. (See e.g., FIG. 22). Each of these LIC coils can facilitate a different range of motion. The close-fitting clamshell configuration of the traditional hand/wrist coil can be designed to provide the highest possible SNR, but it can preclude any form of motion. Alternatively, one can consider using a coil optimized for knee imaging. Such a coil can accommodate moderate wrist motion and finger flexing, at the cost of 3-fold SNR penalty. (See e.g., Table 1 below). If even more complex motions are to be studied using traditional designs, one could opt for an even larger coil, such as a head array, at the price of an even larger SNR penalty. The exemplary HIC glove coil, on the other hand, provides complete freedom of motion while producing almost the same average SNR as the rigid stat-of-the-art hand/wrist coil, despite having only half the number of coil elements. In the exemplary design, yet flexible, HIC elements can be captured by the finger elements on the glove, which demonstrated an 80% SNR improvement compared to the rigid close-fitting hand/wrist coil.

TABLE 1

Quantitative SNR comparison.

|  | head coil (LIC) | knee coil (LIC) | hand/wrist coil (LIC) | glove coil (HIC) |
|---|---|---|---|---|
| hand + wrist | 20% | 29% | 100% | 97% |
| palm | 22% | 36% | 103% | 83% |
| fingertip | 26% | 15% | 74% | 188% |

Average SNR in the hand and wrist, the fingertip, and the palm of the hand, compared to the state-of-the-art 16-channel LIC hand/wrist array.

Exemplary Discussion

The exemplary HIC elements also have a unique strength when deactivated. Multinuclear MR systems focusing on the less-abundant MR-visible nuclei rely on proton-based MR images to visualize the underlying anatomical structure, which utilizes the nesting of multiple RF coils operating at different frequencies. (See e.g., References 30-33). Whereas traditional LICs can only be detuned (e.g., plot 1805) over a narrow bandwidth, leading to residual interactions that distort the RF fields and reduce the SNR, the exemplary HIC elements can detune (e.g., plot 1810) across a wide range of frequencies. (See e.g., graph shown in FIG. 18C).

Figure 33:
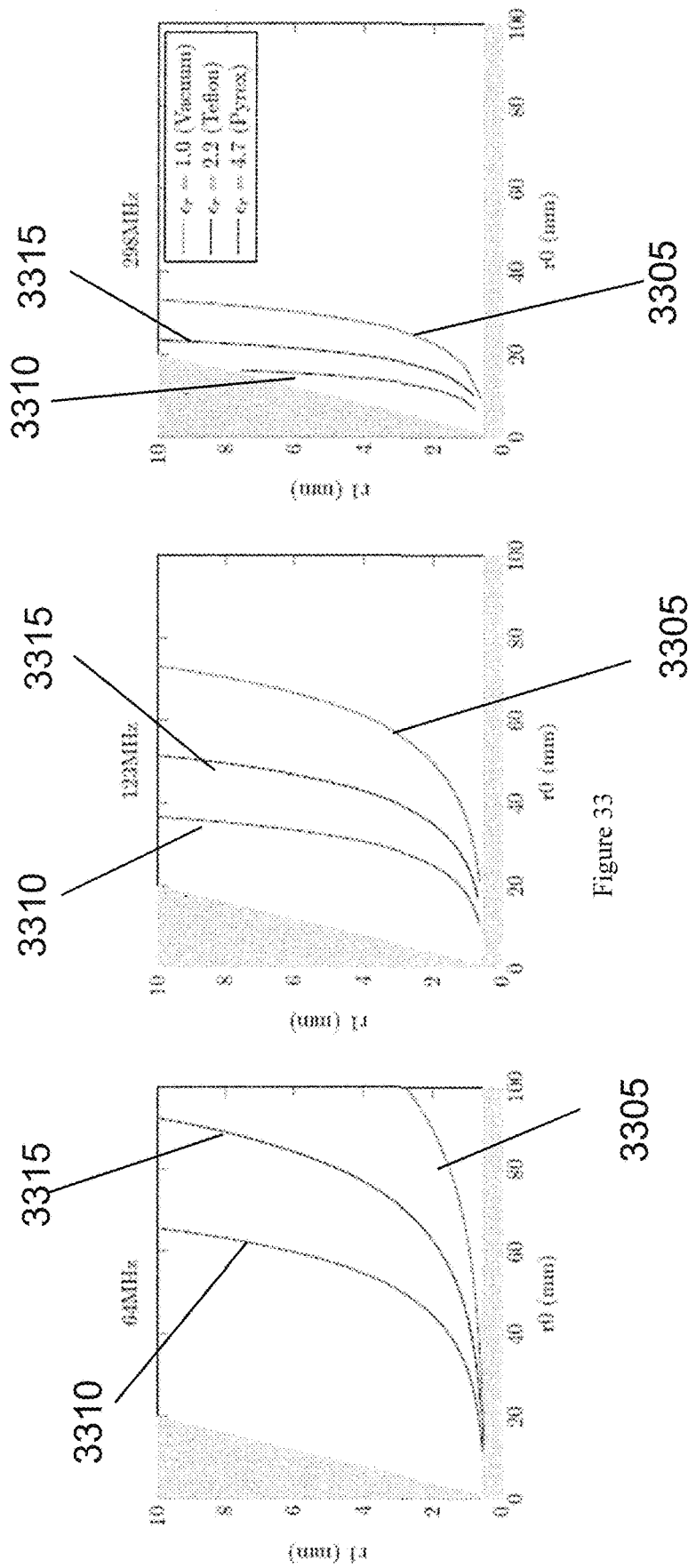
FIG. 33 is a set of graphs illustrating various dimensions (e.g., coil radius r0 and substrate radius r1) for the exemplary HIC coil element using different substrate materials according to an exemplary embodiment of the present disclosure.

Traditional LIC elements come in many shapes and sizes. For example, a dense head coil array at 3 Tesla can use many loop-like elements with diameters as small as about 55 mm. (See, e.g., Reference 36). Cardiac coil arrays, on the other hand, can use rectangular elements as large about 330×270 mm. (See, e.g., Reference 37). Here a circular loop diameter of 80 mm was used for the exemplary phantom comparison. To create significantly smaller HIC elements, a thinner substrate (e.g., reduced r1) or a substrate material with a higher relative permittivity can be used. (See, e.g., FIG. 33). For example, FIG. 33 shows a set of graphs illustrating various dimensions for a Vacuum 3305, Teflon 3310, and Pyrex 3315 (e.g., coil radius r0 and substrate radius r1) for the exemplary HIC coil element using different substrate materials according to an exemplary embodiment of the present disclosure. To create a very large HIC, however, would utilize an impractically thick substrate. For example, to create a HIC with a circumference comparable to other large rectangular loops (See, e.g., Reference 37) utilizes a substrate radius (e.g., r1) of more than about 10 mm. Similarly, adaptation of the exemplary HIC design to other field strengths also can utilize different combinations of dimensions and dielectric materials. (See e.g., FIG. 33).

In addition to the above, skin depth effects can also be considered. In the exemplary HIC design, currents on the inner and outer surface of the outer conductor travel in opposite directions. At about 123 MHz, the skin depth in copper can be approximately 6 µm. The coaxial wrappers used can be much thicker than about 12 µm and can easily support these opposing currents. At very low frequencies, however, this can pose a potential issue. A more practical bottleneck, on the other hand, can be the thickness of the inner conductor. By definition, the inner conductor provides much less surface area to support current. Although a thinner inner conductor could result in HIC elements that can be even more flexible, the additional losses can degrade the coil performance.

The exemplary HIC elements can be size-adjustable and flexible MR coils that can facilitate greater patient comfort and facilitate new areas of research. For example, in addition to facilitating the detailed non-invasive study of joint motion in vivo, and pushing the frontiers of multinuclear MR, HIC-based wearable MR coils can boost the study of brain development, by providing comfortable close-fitting high-density coil arrays that adapt to the subject size. By freeing MR from the electromechanical constraints imposed by traditional low-impedance structures, the exemplary HICs can bring MR to new areas with a premium on adaptability and a simultaneous need for the highest detector performance.

Exemplary Methods

LIC Construction

The exemplary surface coils were constructed as loops about 6 mm in width and about 80 mm in diameter, routed out from a 31 mil single-sided circuit board. (See e.g., FIG. 18A). Four capacitors were evenly distributed on each loop: two fixed about 56 pF capacitors (Series 11, Voltronics Corp., Denville, N.J.) on either side, a variable capacitor on top for tuning, and an about 82 pF fixed capacitor for matching at the port. In addition to transforming the impedance of the coil to the optimal noise matching impedance of the preamplifier (e.g., Siemens Erlangen, Germany), the about 820 capacitor can also form a detuning trap with a positive-intrinsic-negative ("PIN") diode (MA4P4002B-402; Macom, Lowell, Mass., USA). The inductor in the trap was hand-wound. The coils were connected to low input impedance preamplifiers (e.g., Siemens Medical Solutions, Erlangen, Germany). The length of the cable connecting the coil and the preamplifier (e.g., about 24 cm) was carefully adjusted to provide preamplifier decoupling.

HIC Construction

The resonance frequency (f0=ω0/(2π)) of the HIC elements was tuned by adjusting the length of the loops (2πr0), the relative permittivity of the substrate ($\varepsilon_r$), and the ratio between the radius of the outer (r1) and inner radius r2 conductor. (See, e.g., FIGS. 29A-19F and 33).

The admittance as a function of angular frequency (Y(ω)) can be evaluated numerically by estimating the inductive and capacitive impedance of the exemplary HIC element. When tuned, for example, open at the port, the HIC element can be considered as two open ended coaxial stubs of length l connected in series by the center conductor. In this case each arm can add a capacitive impedance (Zc). Thus, for example:

$$Z_c(\omega) = -iZ_0 \cot(\omega l \sqrt{\varepsilon_r}/c) \quad (1)$$

where Z0 the characteristic impedance of the coaxial line.

For a co-axial cylindrical conductor, the characteristic impedance can be given by, for example:

$$Z_0(\omega) = \sqrt{\frac{R + i\omega L_{coax}}{G + i\omega C_{coax}}} \quad (2)$$

where R can be the resistance per unit length, G can be the conductance per unit length of the dielectric, Lcoax can be the inductance per unit length, and Ccoax can be the inductance per unit length. Assuming, R=0 and G=0, $$Z_0 = \frac{1}{2\pi}\sqrt{\frac{\mu_0}{\varepsilon_0 \varepsilon_r}} \ln\left(\frac{r1}{r2}\right)$$

can be found, where μ0 can be the permeability of free space.

The inductive impedance of the HIC can be approximated by the self-inductance of the loop of similar size. Thus, for example:

$$Z_L(\omega) = i\omega\mu_0 r_0\left(\ln\left(\frac{8r_0}{r_1}\right) - 2\right) \quad (3)$$

Thus, the admittance (Ytuned=1/Z) of the HIC can be approximated by, for example:

$$Y(\omega) = (Z_L(\omega) + 2Z_C(\omega))^{-1} \quad (4)$$

where the factor 2 can account for the two open ended stubs in the coil.

The above equations can be used to numerically explore the design space of exemplary HIC elements. The high impedance nature of this design can be more clearly illustrated by its equivalent circuit (e.g., a parallel resonator). Thus, for example:

$$Z_{HIC}(\omega) = \frac{2Z_C(\omega)(R + Z_L(\omega))}{R + Z_L(\omega) + 2Z_C(\omega)} \quad (5)$$

where R=Rcoil+Rload. If it is assumed that the coil can be unloaded (Rload=0), for example, that no phantom or subject can be in range, and that the coil losses can be neglected (Rcoil=0), the following can be found:

$$\lim_{\omega \to \omega_0} Z_{HIC}(\omega) = \infty \quad (6)$$

because ZL(ω)+2ZC (ω) tends to 0 as ω approaches the resonance frequency. R can be in the order of 10Ω, which can lead to the observed finite but high input impedance of approximately 2 kΩ.

Computer-aided design of the coil substrate was performed in Solidworks (e.g., Dassault Systems, USA). The substrate was printed on a Fortus 360mc 3D printer (e.g., Stratasys, US) using polycarbonate, with a relative permittivity of εr=2.2. The substrate for each coil was printed in two parts. The inner conductor was made from hand-wound copper threads (e.g., 13 strands, final thickness 1 mm) and the conductive mesh was taken from a commercial coaxial cable (e.g., RG58). First, the inner conductor was placed in the central grove of the substrate. The structure was then capped by adding the second half on top. The coaxial braid was placed around the substrate and stretched out to form a tight coaxial enclosure, taking care that the two halves of the dielectric properly encased the central conductor. Heat shrink tubing around the coaxial structure was used to insulate and protect the main structure. The radius (r0) of the completed HIC loop was about 40 mm, the radius of the cylindrical inner conductor (r2) was about 0.5 mm, and the substrate thickness was about 0.7 mm, and the diameter of the coaxial structure before shrink-wrapping was about 2.4 mm (r1=1.2 mm). (See, e.g., FIGS. 19A-19F).

Figure 34B:
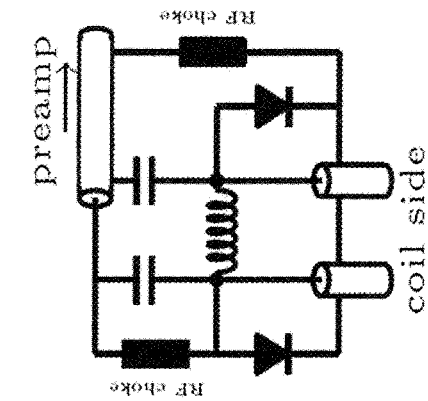
FIG. 34B is an exemplary schematic diagram of the corresponding layout to FIG. 34A according to an exemplary embodiment of the present disclosure.
Figure 34A:
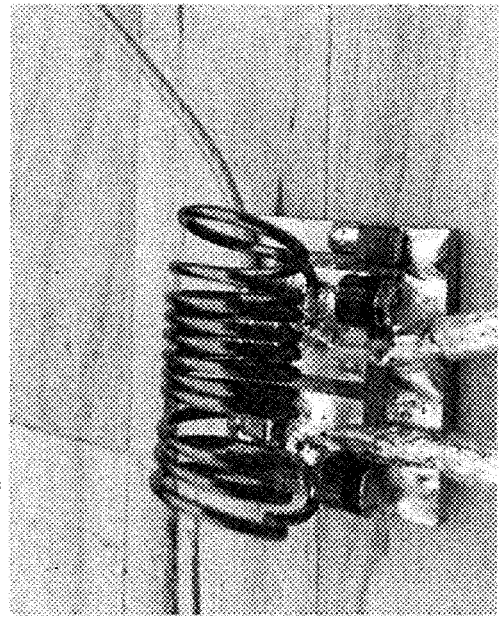
FIG. 34A is a an exemplary photo of an exemplary HIC interface board according to an exemplary embodiment of the present disclosure.

The coil was then mounted on a 62 mil single-sided circuit board (e.g., 10 mm×18 mm) made with the same circuit router used to create the LICs described above. The two ends of the outer conductor were connected through the board, and a LC circuit was connected to the two ends of the inner conductor to transform the high impedance of the coil to the optimal noise matching of the preamp. (See e.g., FIG. 19B). The cable length connecting the coil and preamplifier (e.g., 22 cm) was adjusted to create a low impedance at the port. Here, the port can be defined as the two leads attached to the inner conductor of the coil. The combined circuit formed by the interface board, pre-amplifier and connecting cables effectively creates a short between the two ends of the inner conductor. This can be the exact opposite of preamplifier decoupling in traditional low impedance coils, for which a high impedance can be arranged at the port. A detailed picture of the interface board and an associated schematic diagram is shown in FIGS. 34A and 34B.

The above-described impedance transformation can be eliminated when using a high impedance metal-oxide-semiconductor field-effect transistor ("MOSFET"). Gallium Arsenide MOSFETs, for example, have an optimal noise figure at about 1 to 2 kΩ (e.g., similar to the intrinsic impedance of the exemplary HICs). Although removing the transformation network could help to further improve the SNR obtained using the exemplary HIC design, the same preamplifiers were used for both LIC and HIC coils to avoid any possible bias due to variations in the preamplifier design.

To detune the coil during transmit, two PIN diodes were placed between the leads on the inner and outer conductors. When a direct current ("DC") can be provided, the PIN diodes short the two ends of the inner conductor to the outer conductor (e.g., forward bias). During receive, the stray capacitance of the PIN diode can be incorporated into the matching network.

In addition to the 3D printed design, a HIC was also implemented using commercially available coaxial cable. RG178 was selected: a 50Ω cable with dimensions similar to the 3D printed coil design. The RG178 HIC was molded into the same shape as the 3D printed HIC by strapping it to a thin plastic sheet. The same interface, preamplifier, and detuning configuration was used.

When building the HIC elements, two or more mechanisms can be used to adjust for imperfections and variations in the material specifications. Firstly, it can be advisable to cut/print the coaxial stubs slightly longer than can be nominally needed, so that they can be cut to size on the bench. Alternatively, it can also be possible to include a tuning mechanism on the interface board. When the dimensions of the HIC can be exactly right, the inductance and distributed capacitance can cancel each other. In this situation, the impedance of the coil has no imaginary part. When the coil can be too long, a capacitive imaginary component can appear, which can be compensated by an inductor parallel to the residual capacitance. Similarly, when the coil can be too short, an inductive imaginary component can appear, which can be compensated with a capacitor parallel to the residual inductance.

Exemplary Simulations

Figure 35:
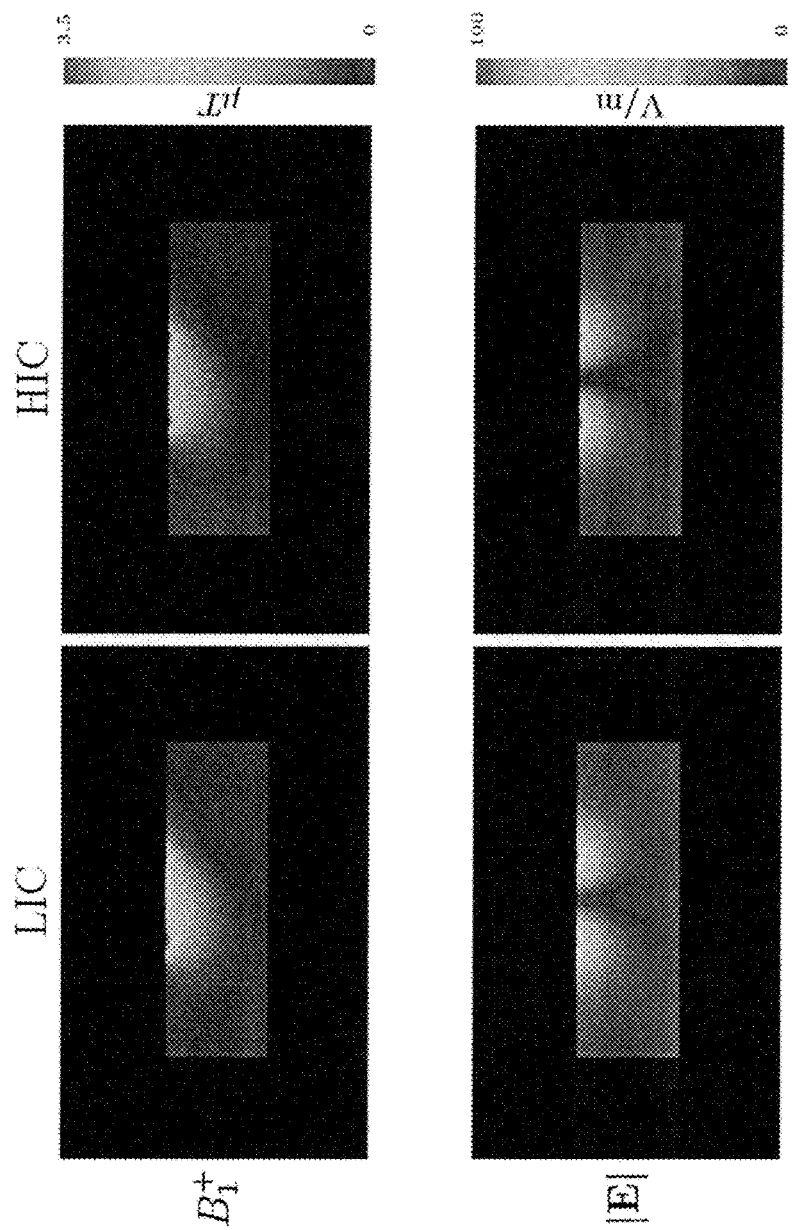
FIG. 35 is a set of exemplary images illustrating Simulated $\|E\|$ and B1+ fields in a large cuboid phantom according to an exemplary embodiment of the present disclosure.

To visualize the current distribution on the exemplary HIC element (e.g., 8 cm diameter), the coil was modeled in CST Microwave Studio (e.g., Darmstadt, Germany). Leveraging the reciprocity relation between transmit and receive fields, the coil was driven using a high impedance voltage source at the port (e.g., input power 0.5 W). The preamplifier and detuning circuit were excluded from the simulation. The coil was placed about 5 mm above a large cuboid phantom (e.g., 317×317×104 mm, σ=0.53). Radiative boundary conditions were placed at about a 100 mm distance from the phantom and coil arrangement. The surface current density distributions were exported and analyzed in Mathematica (e.g., Wolfram Research, Champaign, Ill.). In addition, an about 8 cm diameter LIC, driven using a low impedance voltage source at the port (e.g., input power 0.5 W), was also simulated. For comparison, the |E| and ||B+| are shown in FIG. 35.

Figure 36:
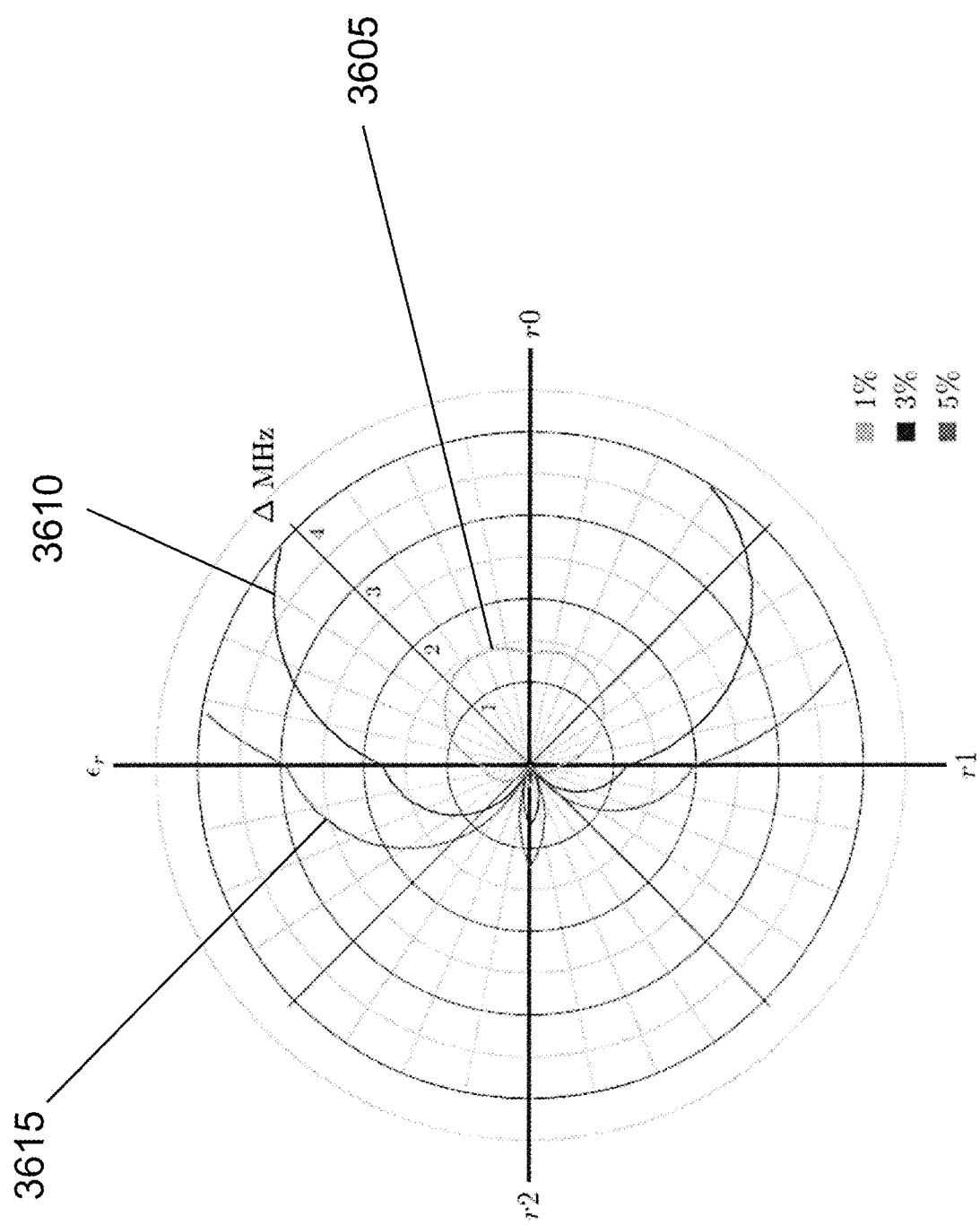
FIG. 36 is an exemplary graph illustrating the deviation from the target frequency as a function of variation in material properties/dimensions for an 80 mm diameters HIC according to an exemplary embodiment of the present disclosure.

In addition, Eq. 4 was used to numerically evaluate the landscape of possible coil sizes for use in a Proton MRI setup operating at 1.5, 3.0, and 7.0 Tesla. (See e.g., FIG. 33). Similarly, the sensitivity of the resonance frequency to variations in material properties and design parameters were evaluated. (See e.g., FIG. 36). For example, FIG. 36 shows material properties of 1% (e.g., element 3605), 3% (e.g., element 3610) and 5% (e.g., element 3615).

Exemplary Bench Experiments

A homemade double probe was attached to a network analyzer (e.g., Agilent, model E5071C) and the overlap was adjusted to eliminate mutual coupling (e.g., less than −70 dB). To provide a baseline, the coupling between the two elements in the double probe (S1,2) was measured in free space far from any object, over a frequency range of about 20 MHz to about 200 MHz. Subsequently, a LIC element was placed underneath the double probe, and the S1,2 was measured in the tuned and detuned states. The same process was repeated using an exemplary HIC element.

To determine how the impedance at the port can influence the traditional current suppression mechanism of preamplifier decoupling for LICs and the exemplary reversed preamplifier decoupling for HICs, a variable resistor was placed across the port of the coil, and the S1,2 was measured using the double probe setup. The S1,2 was recorded at the Proton Larmor frequency of interest (e.g., about 123 MHz), and was plotted as a function of impedance at the port. (See e.g., FIG. 18D). In addition, the S1,1 of both HIC and LIC coils were measured and the Smith-Charts were plotted. (See e.g., FIGS. 25A and 25B).

Figures 26A, 26B:
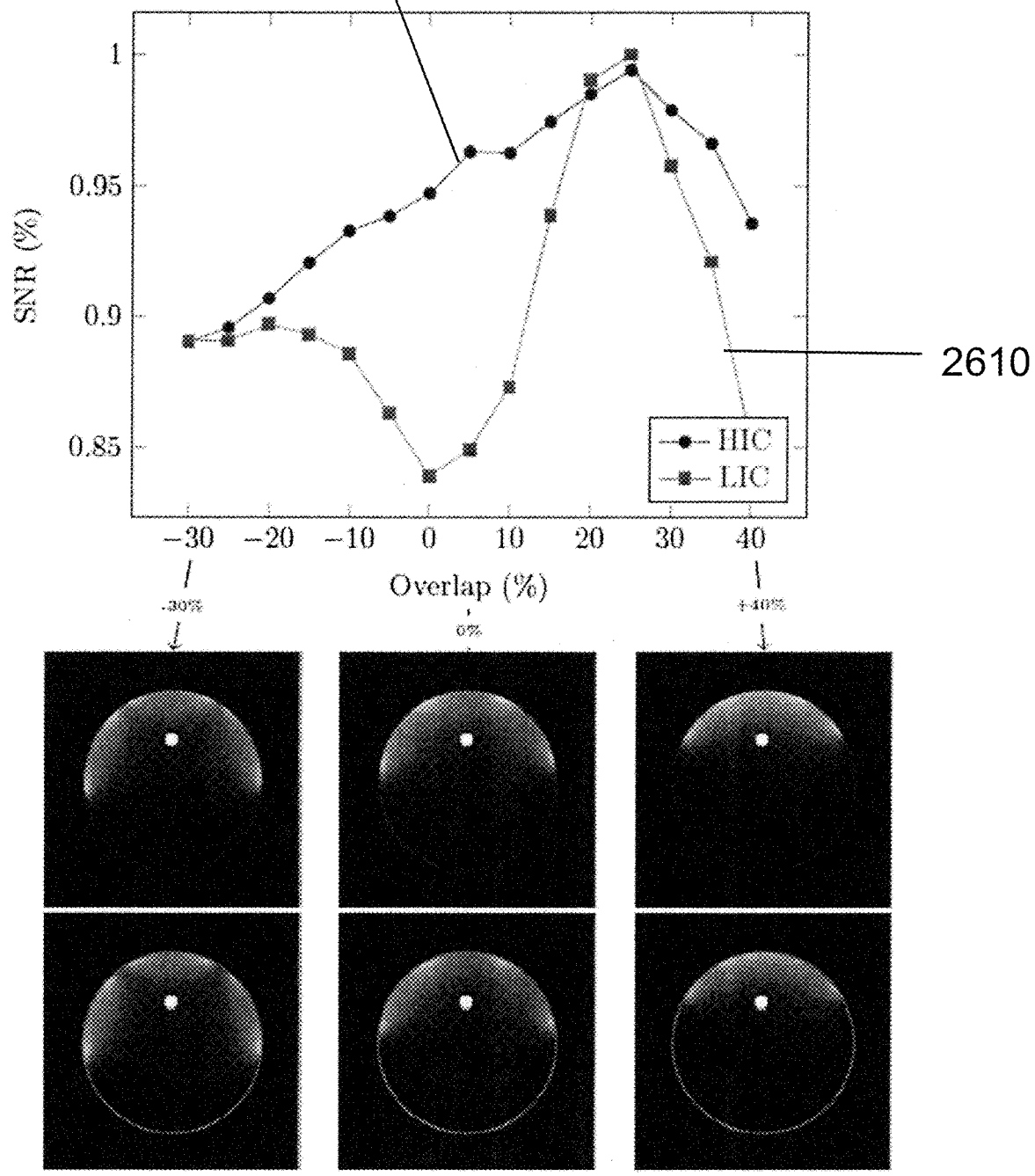
FIG. 26A is an exemplary graph illustrating the evaluation of SNR degradation due to coupling between neighboring coil elements as a function of coil overlap on a cylindrical surface according to an exemplary embodiment of the present disclosure.
FIG. 26B is an exemplary set of generated MR images shoeing the combined signal images according to an exemplary embodiment of the present disclosure.

FIG. 26A shows the evaluation of SNR degradation due to coupling between neighboring coil elements as a function of coil overlap on a cylindrical surface (e.g., 16.9 cm diameter). HIC measurement 2605 and LIC measurements 2610 lines show the SNR at 4.2 cm below the center coil in an exemplary three-coil arrangement. The overlap between coils is varied between −30 and +40%, where the % overlap is computed from the element diameter. The MR shown in FIG. 26B illustrate the combined signal images at −30, 0 and +40% overlap with outlines superimposed on the MR images mark the edges of the phantom. The white dot indicates the position of the SNR measurement. The reduced SNR degradation for the LICs on the cylindrical surface can be explained by the increased orthogonality of the coil elements as the angle increases (e.g., at −30% overlap, the coils are almost at a 90° angle to one another).

Exemplary Phantom Experiments

To determine the interaction between coils and its effect on the SNR, a large cuboid phantom (e.g., 317×317×104 mm) was constructed. The phantom was filled with distilled water, doped with about 2.5 g/L Sodium chloride (NaCl, Sigma-Aldrich, St Louis, Mo., USA) and 50 mg/L manganese (II) chloride tetrahydrate (Cl2Mn 4H20, Sigma-Aldrich, St Louis, Mo., USA). The conductivity of the liquid was measured using an Agilent dielectric probe (e.g., model 85070E) attached to a network analyzer (e.g., model E5071C) calibrated using an eCal module (e.g., model 85093C). The conductivity was found to be about 0.53 S/m.

Before the SNR experiments, the losses in the coil interface and receive chain were evaluated. A single LIC reference coil was placed on the center of the phantom and connected to the first port on the coil interface. Two gradient recalled echo ("GRE") images, axially through the center coil, were acquired, one signal image (e.g., flip angle=25 degrees) and one noise image (e.g., flip angle=0 degrees). Sequence parameters were as follows: 3 ms echo time, 200 ms repetition time, 256×256 matrix, 384×384 mm field of view, 5 mm slice thickness, and 300 Hz/pixel readout bandwidth. These measurements were performed for each port on the interface (e.g., without moving the coil or interface). The relative signal to noise ratio between receive channels was calculated and incorporated into the subsequent SNR analysis.

Three series of experiments were performed. The first series of experiments was designed to show the effect of signal coupling between elements during receive. Three identical LICs were placed side by side on top of the phantom (e.g., approximately 5 mm apart). Four GRE images were acquired: one using all three loops simultaneously, and one for each coil element individually with the other coil elements detuned (e.g., same sequence parameters described above). The same experiment was repeated using 3 HICs placed side by side (e.g., approximately 5 mm apart).

The same axial slice through the center of all three loops was used throughout the experiment.

The second series of experiments was designed to quantify the effect of coil overlap on the SNR. Again, three LIC elements were placed side by side, and this time the overlap between coil elements was varied between about −40% and about +40%, in increments of about 5%, without moving the center element. The % overlap was calculated based on the diameter of the coil element. For example, a 25% overlap corresponds to a 12 cm center-to-center distance between neighboring elements. For each overlap, two gradient echo images were acquired using all three loops simultaneously (e.g., same sequence parameters as before), once using a flip angle of 25 degrees, to obtain the signal, and once using a 0 degree flip angle, to collect a noise measurement. In addition, a B+ map was acquired using the pre-saturation turbo flash method. (See e.g., Reference 38). The same series of experiments was repeated using three identical HICs. The same axial slice through the center of all three loops was used throughout all measurements. SNR maps were calculated in Matlab as outlined by Kellman & McVeigh. (See e.g., Reference 39). Receive profiles were derived using a body coil reference image (e.g., same sequence parameters), and the optimal SNR coil combination was used to combine the individual images. (See e.g., Reference 4). The $B_1^+$ maps were used to normalize the SNR and remove transmit field variations due to dielectric effects inside the phantom.

Phantom experiments similar to those described earlier were also performed on a cylindrical phantom (16.9 cm diameter) filled with a liquid of identical composition ($\sigma$=0.53 S/m) to that filling the rectangular phantom. The support of the cylindrical phantom did not facilitate coils to be placed beyond the centerline, thus limiting the maximum center to center distance between coils (e.g., measured along the circumference of the cylinder) to about 11.2 cm (e.g., −30%). Because it was more difficult to place the coils accurately on the cylindrical surface, the whole series of experiments was performed twice and the mean of the two series is shown in FIG. 20A, with the resulting images shown in FIG. 20B.

The SNR obtained with a single LIC was also measured using a single 3D printed HIC, and a single RG178 HIC element (e.g., same sequence parameters).

All experiments were performed on a 3 Tesla MR system (e.g., Skyra, Siemens, Erlangen, Germany), using the body coil for transmission.

Exemplary Glove Coil Construction

Figure 37:
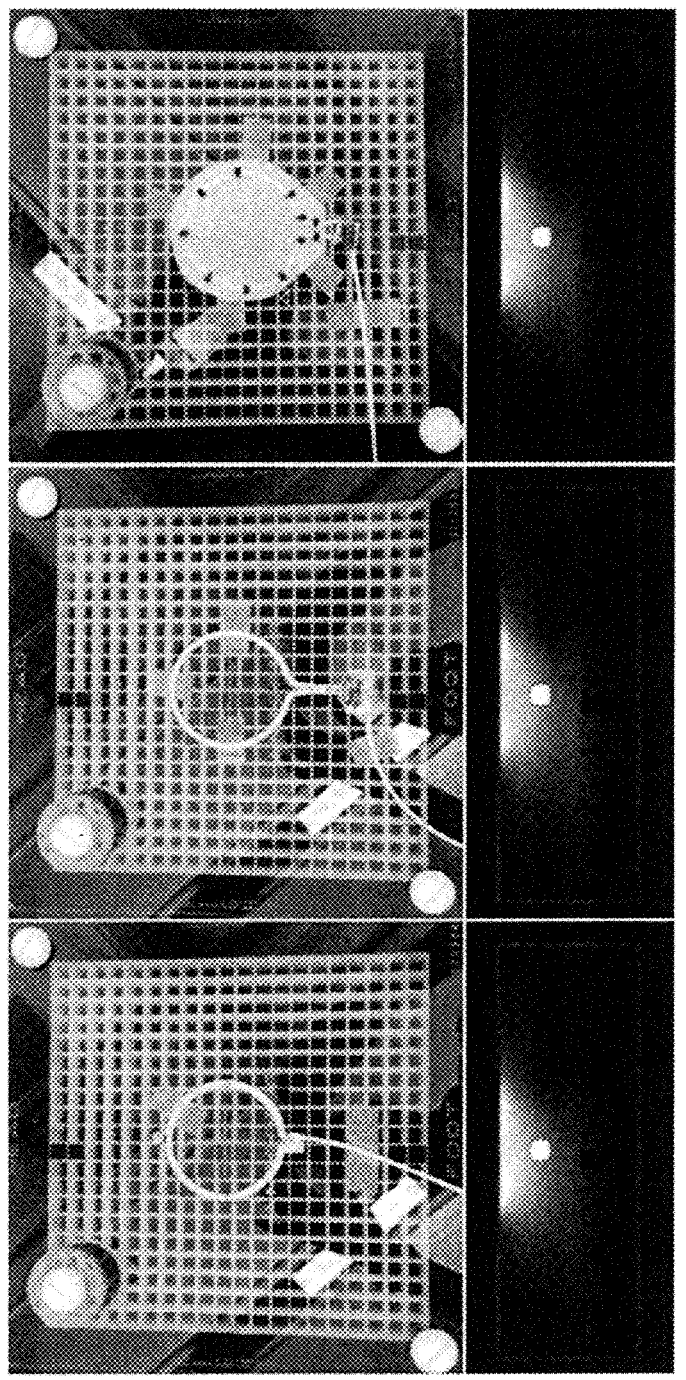
FIG. 37 is a set of images of the exemplary conductor and corresponding evaluation of the SNR relative to a traditional 9 cm low impedance coil element according to an exemplary embodiment of the present disclosure.

Extra-long black cotton gloves were used to construct the glove coil. Although the exemplary 3D printed coils can be flexible, it may not be clear how the 3D printed polycarbonate material can withstand repeated bending. Instead, an RG178 coaxial cable was used, which has properties similar to the exemplary 3D printed design. (See, e.g., FIG. 37). The RG178 contains a durable Teflon substrate seamlessly encasing the inner conductor. Heat shrink was used to insulate the break in the conductive braid on the far end of the coil. The same interface boards as described above were used to mount the detuning circuit and the impedance transformation circuit. Five coils were stitched along the contours of the fingers, one for each finger. The inductance of the HIC can also depend on the shape of the coil. (See, e.g., FIG. 32). When the exemplary HIC elements can be bent in the glove coil, for example when a finger can be curled, the frequency can change slightly. Therefore, the finger coils were tuned in a slightly bent configuration. These five coils have a slightly larger inductance due to their elongated shape, leading to a circumference of about 315 mm. Two additional coils were stitched on the top of the glove, one centered on the hand, and the second centered on the wrist. The final coil was stitched on the bottom of the glove, partially covering the wrist and hand. These three circular coils have a circumference of about 252 mm. All elements were tuned to the same resonance frequency.

The preamplifiers (e.g., Siemens, Erlangen, Germany) were mounted on a bracelet fashioned out of acrylic plastic and connected to the MR system using a vendor specific ODU connector (e.g., ODU-USA, Camarillo, Calif., USA). Two cable traps were placed on the cable connecting the preamplifiers to the scanner. The glove coils were connected to the preamplifiers through a shielded cable trap using the same thin coaxial cables found in the cable provided by ODU. The cable length from the preamp to the cable trap was about 12 cm and from the cable trap to the HIC elements about 22 cm.

Before in vivo experiments, the detuning circuits were tested on the bench and using phantom experiments in the scanner. During the phantom experiments, the difference in transmit reference voltage, with and without the glove coil present, was found to be less than about 1%, and no noticeable distortions were observed in the transmit field distribution. An infrared camera (e.g., E60bx, FLIR Systems, Wilsonville, USA) was used to image the surface temperature of the glove and interface before and after about a 15 min interval of high applied power (e.g., 100% specific absorption rate). No significant temperature differences were observed ($\Delta T \ll C°$).

Exemplary In Vivo Experiments

High resolution T1 weighted images of the left hand were acquired at 3 Tesla using the body coil for transmission and the glove coil for reception. The volunteer was imaged in a prone position on the scanner bed, with the left hand stretched out in front of her. In the first experiment, the hand was placed flat on the table. Low resolution GRE images were used to localize the hand inside the scanner. High resolution (e.g., 250 μm) T1 weighted turbo spin echo ("TSE") images of the left hand were acquired in coronal and sagittal planes (e.g., TSE, 1024×786 matrix, 256×192 mm field of view, 2 mm slice thickness, Turbo factor 2, excitation/refocusing angle of 90/180 degrees, TR=400 ms, TE=15 ms, total scan time 2 min:37 sec). In addition, about 150 μm resolution images were acquired in sagittal only (e.g., TSE, 2048×512 matrix, 303×76 mm field of view, 2 mm slice thickness, Turbo factor 2, excitation/refocusing angle of 90/180 degrees, TR=400 ms, TE=15 ms, total scan time 1 min:42 sec) In the second experiment, with the same general setup, the volunteer was holding a peach. After localization, a second series of coronal and sagittal T1 weighted TSE images was acquired (e.g., same sequence parameters as before). In addition, a proton density weighted 3D GRE dataset was acquired covering only a single finger (e.g., 0.5 mm isotropic, 512×64×104 matrix, 256×32×52 mm field of view, TR=12 ms, TE=5 ms, 10 degree flip angle, total scan time 1 min 20 sec).

A second volunteer was scanned at 3 Tesla to capture the dynamics of a hand moving inside the scanner. The volunteer was imaged in a prone position on the scanner bed, with the left arm in front. During the first experiment, the volunteer was asked to move her fingers as if playing piano or typing. While the subject moved, about 4000 radial projections were acquired in a coronal plane through the hand (e.g., Golden angle radial GRE, 0.8×0.8 mm, 192×192 matrix, 160×160 mm field of view, 2.5 mm slice thickness, TR=6.5 ms, TE=3.5 ms, total acquisition time 25 seconds).

From these about 4000 projections, about 260 images were reconstructed at about 10 frames per second, using a sliding window reconstruction spanning about 100 projections. (See e.g., Reference 40).

In a second experiment, a peach was placed within reach of the volunteer, on top of the patient table. An axial slice was positioned through the center of the peach. Because there were no coil elements on the peach, the laser positioning system on the scanner was used to locate the appropriate slice. During dynamic MR data acquisition (e.g., using the same golden angle radial sequence as before), the subject reached out to grasp the peach.

Finally, a third volunteer was scanned using both the HIC glove coil and three LIC-based phased arrays. (See e.g., FIG. 22). Each of the LIC-based coils (e.g., hand, knee and head array) was built around a different plastic former. The 16-channel hand/wrist coil (Siemens Healthineers, Erlangen, Germany) was constructed on a tight-fitting clamshell, which leaves no space for the wrist, hand or fingers to move. The 15-channel knee coil (e.g., QED, Mayfield Village, Ohio, USA) was constructed around a 154 mm cylindrical shell. The 20-channel head coil (e.g., Siemens Healthineers, Erlangen, Germany) was constructed around an about 232 mm domed cylindrical shell. SNR measurements were performed using the same tools described above, only this time the FOV was adjusted to about 256 mm and 4 averages of the body coil images were used to estimate the receive profiles. The knee coil uses a local transmit coil. In this case, the sum-of-squares image was used as a reference to construct the receive profiles. The results of the SNR comparison were further quantified by delineating the hand+wrist, palm of the hand, and fingertip in the SNR maps and calculating the average SNR value in each of these regions. The results were normalized to the average SNR observed with the state-of-the-art LIC hand/wrist coil. (See, Table 1 above). In addition, a sagittal 250 µm-resolution T1 weighted TSE image was acquired (using the same sequence parameters as described above.

An exemplary coil arrangement can be provided, which can include, for example an inner coil(s), a substrate(s), and an outer coil(s) which can be segmented from the inner coil(s) via the substrate(s). The substrate(s) can include a capacitor(s). The outer coil(s) can be configured to shield a current flowing through the inner coil(s). A potential of two ends of the inner coil(s) can be equal based on a ground. A detuning arrangement(s) can be coupled to at least one of the inner coil(s) or the outer coil(s). A self-resonant arrangement(s) can be coupled to the inner coil(s) or the outer coil(s).

In some exemplary embodiments of the present disclosure, the inner coil(s) and the outer coil(s) can be flexible. The coil arrangement can be configured to be used at 3 Tesla or 7 Tesla. The coil arrangement can be integrated into (i) a hat, or (ii) a blanket. The outer coil(s) can be segmented into at least two symmetrical pieces.

In some exemplary embodiments of the present disclosure, the coil arrangement can have a high intrinsic impedance. The coil arrangement can be configured to use the high intrinsic impedance to reduce inductive coupling. The coil arrangement can be configured to be used at multiple frequencies.

Figure 38:
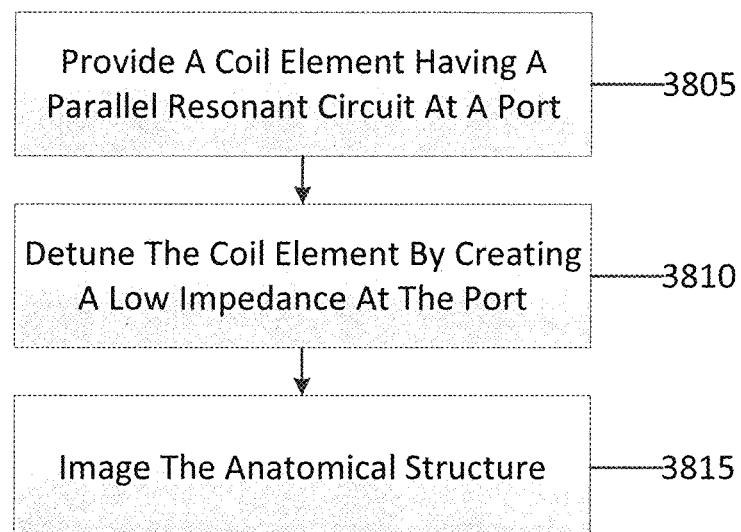
FIG. 38 is an exemplary method for imaging an anatomical structure according to an exemplary embodiment of the present disclosure.

FIG. 38 shows an exemplary method 3800 for imaging an anatomical structure according to an exemplary embodiment of the present disclosure. For example, at procedure 3805, a coil element can be provided which has a parallel resonant circuit at a port. At procedure 3810, the current on the at least one coil element can be reduced by providing a low impedance at the port. At procedure 3815, the anatomical structure can be imaged using the coil element.

Figure 39:
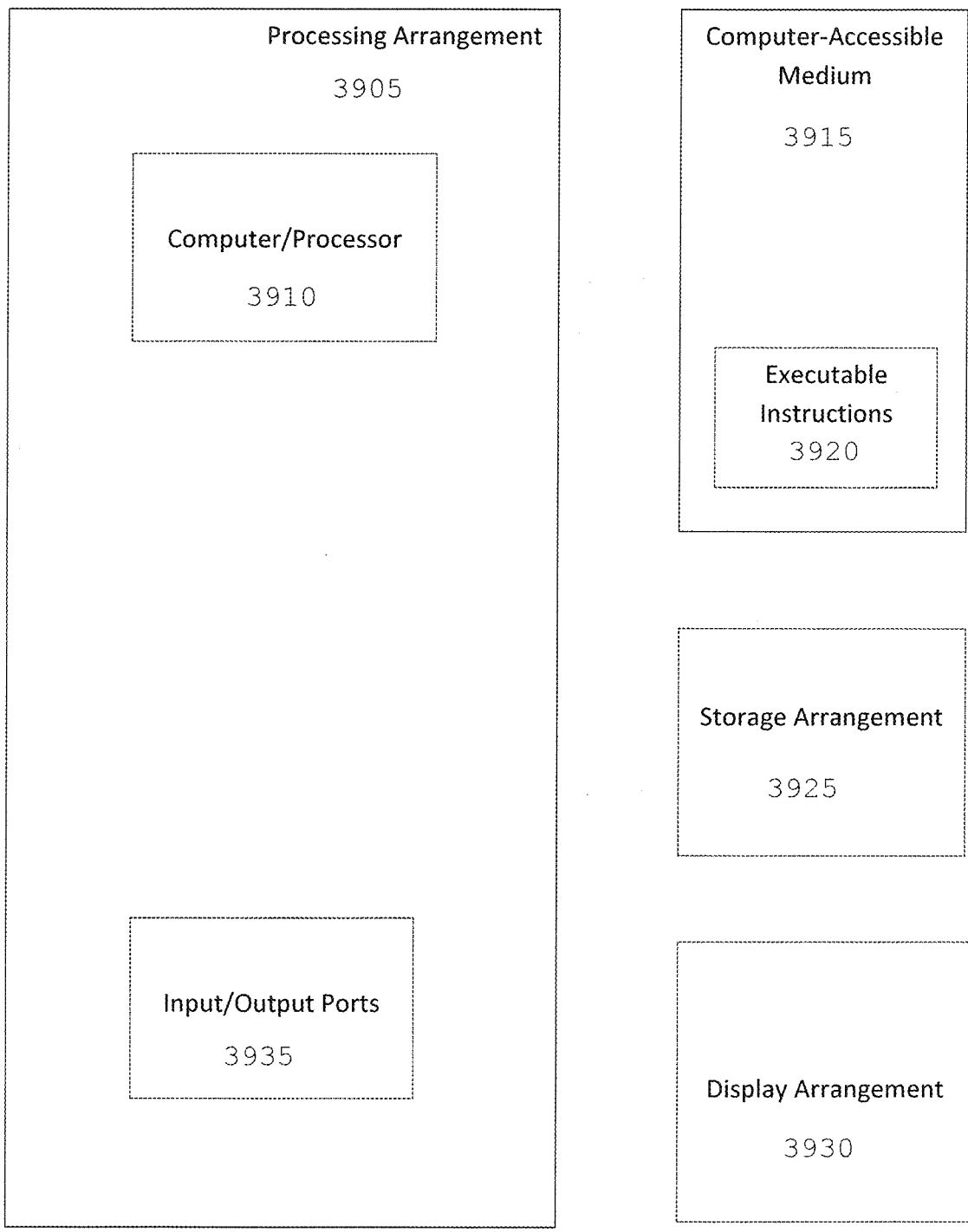
FIG. 39 is an illustration of an exemplary block diagram of an exemplary system in accordance with certain exemplary embodiments of the present disclosure.

FIG. 39 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 3905. Such processing/computing arrangement 3905 can be, for example entirely or a part of, or include, but not limited to, a computer/processor 3910 that can include, for example one or more microprocessors, and use instructions stored on a computer-accessible medium (e.g., RAM, ROM, hard drive, or other storage device).

As shown in FIG. 39, for example a computer-accessible medium 3915 (e.g., as described herein above, a storage device such as a hard disk, floppy disk, memory stick, CD-ROM, RAM, ROM, etc., or a collection thereof) can be provided (e.g., in communication with the processing arrangement 3905). The computer-accessible medium 3915 can contain executable instructions 3920 thereon. In addition or alternatively, a storage arrangement 3925 can be provided separately from the computer-accessible medium 3915, which can provide the instructions to the processing arrangement 3905 so as to configure the processing arrangement to execute certain exemplary procedures, processes, and methods, as described herein above, for example.

Further, the exemplary processing arrangement 3905 can be provided with or include an input/output arrangement 3935, which can include, for example a wired network, a wireless network, the internet, an intranet, a data collection probe, a sensor, etc. As shown in FIG. 39, the exemplary processing arrangement 3905 can be in communication with an exemplary display arrangement 3930, which, according to certain exemplary embodiments of the present disclosure, can be a touch-screen configured for inputting information to the processing arrangement in addition to outputting information from the processing arrangement, for example. Further, the exemplary display 3930 and/or a storage arrangement 3925 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following reference(s) are hereby incorporated by reference in their entireties:

[1] Bloch F., Nicodemus D., Staub H. A., Quantitative Determination of the Magnetic Moment of the Neutron in Units of the Proton Moment. Phys. Rev., 1948; 74:1025.

[2] Lauterbur P. C., Image Formation by Induced Local Interactions: Examples Employing Nuclear Magnetic Reso-nance. Nature 1973; 242:190-191.

[3] Mansfield, P., Grannell, P. K., NMR 'diffraction' in solids? Phys. C. Solid. Stat., 1973; L422-L426.

[4] Roemer P. B., et al., The NMR Phased Array. Magn. Reson. Med., 1990; 16:192-225.

[5] Wang J., Reykowski A., Dickas J., Calculation of the signal-to-noise ratio for simple surface coils and arrays of coils. IEEE Trans. Biomed. Eng. 1995; 42:908-917.

[6] Ocali O., Atalar E., Ultimate intrinsic signal-to-noise ratio in MRI. Magn. Reson. Med., 1998; 39:462-473.

[7] Schnell W., Renz W., Vester M., Ermert H., Ultimate Signal-to-Noise Ratio of Surface and Body Antennas for Magnetic Resonance Imaging. IEEE Trans. Antennas. Propag. 2000; 48:418-428.

[8] Ohliger M. A., Grant A. K., Sodickson D. K., Ultimate intrinsic signal-to-noise ratio for parallel MRI:Electro-mag-netic field considerations. Magn. Reson. Med., 2003; 50:1018-1030.

[9] Wiesinger F., Boesiger P., Pruessmann K. P., Electrodynamics and ultimate SNR in parallel MR imaging. Magn. Reson. Med., 2004; 52:376-390.

[10] Lattanzi R., et al., Performance evaluation of a 32-element head array with respect to the ultimate intrinsic SNR. NMR Biomed 2010; 23:142-151.

[11] Lattanzi R, Sodickson D K. Ideal current patterns yielding optimal signal-to-noise ratio and specific absorption rate in magnetic resonance imaging: computational methods and physical insights. Magn. Reson. Med., 2012; 68:286-304.

[12] Wiggins G. C., et al., 96-Channel receive-only head coil for 3 Tesla: design optimization and evaluation. Magn. Reson. Med., 2009; 62:754-62.

[13] Schmitt M, et al. A 128-channel receive-only cardiac coil for highly accelerated cardiac MRI at 3 Tesla. Magn. Reson. Med., 2008; 59:1431-1439.

[14] Fujita H., Zheng T., Yang X., Finnerty M. J., Handa S., RF surface receive array coils: the art of an LC circuit. J. Magn. Reson. Imaging, 2013; 38:12-25.

[15] Kurs A., et al., Wireless Power Transfer via Strongly Coupled Magnetic Resonances. Science, 2007; 317:83-86.

[16] Tierney B., Grbic A., Planar shielded-loop resonators for wireless non-radiative power transfer. IEEE Antennas and Propagation Society International Symposium (AP-SURSI). 2014; DOI:10.1109/APS.2013.6711080.

[17] Information on materials and methods in the supplements following the main body of the paper.

[18] Gonord P, Kan S, Leroy-Willig A. Parallel-Plate Split-Conductor Surface Coil: Analysis and Design. Magn. Reson. Med., 1988; 6:353-358.

[19] Serfaty S, Haziza N, Darrasse L, Kan S. Multi-Turn Split-Conductor Transmission-Line Resonators. Magn. Reson. Med. 1997; 38:687-689.

[20] Frass-Kriegl R, Laistler E, Hosseinnezhadian S, Schmid A I, Moser E, Poirier-Quinot M, Darrasse L, Ginefri J-C. Multi-turn multi-gap transmission line resonators: Concept, design and first implementation at 4.7T and 7T. J. Magn. Reson. 2016; 273:65-72.

[21] Corea J. R, et al., Screen-printed flexible MRI receive coils. Nat. Commun. 2016; 7:10839.

[22] Vasanawala A., et al, Development and Clinical Implementation of Very Light Weight and Highly Flexible AIR Technology Arrays. Proc. Intl. Soc. Mag. Reson. Med., 2017; 0755

[23] Stormont R, et al., Reimagining Flexible Coil Technology. SIGNA, 2017; Spring: 69-71.

[24] Stengaard A., Planar Quadrature Coil Design Using Shielded-Loop Resonators. J. Magn. Reson., 1997; 125: 84-91.

[25] Sodickson D. K., Manning W. J. Simultaneous acquisition of spatial harmonics (SMASH): fast imaging with radiofrequency coil arrays. Magn. Reson. Med., 1997; 38:591-603.

[26] Pruessmann K., Weiger M, Scheidegger M B, Boesiger P. SENSE: sensitivity encoding for fast MRI. Magn. Reson. Med., 1999; 42:952-962.

[27] Griswold M., et al., Generalized autocalibrating partially parallel acquisitions (GRAPPA). Magn. Reson. Med., 2002; 47:1202-1210.

[28] Larkman D. J., Hajnal J. V., Herlihy A. H., Coutts G. A., Young I. R., Ehnholm G. Use of multicoil arrays for separation of signal from multiple slices simultaneously excited. J Magn. Reson. Imaging. 2001; 13(2):313-317.

[29] Setsompop K., et al., Blipped-controlled aliasing in parallel imaging for simultaneous multislice echo planar imaging with reduced g-factor penalty. Magn. Reson. Med., 2012; 67:1210-1224.

[30] Schnall M. D., Harihara Subramanian V., Leigh J. S., Chance B. A new double-tuned probed for concurrent 1H and 31P NMR. J. Magn Reson. 1985; 65:122-129.

[31] Avdievich N I, Hetherington H P. 4 T Actively detuneable double-tuned 1H/31P head volume coil and four-channel 31P phased array for human brain spectroscopy. J Magn Reson. 2007; 186:341-346.

[32] Brown R., et. al., Design of a nested eight-channel sodium and four-channel proton coil for 7T knee imaging. Magn. Reson. Med., 2013; 70:259-268.

[33] Shajan G., et al., Three-layered radio frequency coil arrangement for sodium MRI of the human brain at 9.4 Tesla. Magn. Reson. Med., 2016; 75:906-916.

[34] Kriegl R, et al., Novel inductive decoupling technique for flexible transceiver arrays of monolithic transmission line resonators. Magn. Reson. Med., 2015; 73:1669-81.

[35] Hosseinezhadian S, et al., A Flexible Transceiver Array for 7 T Cardiac MRI: First Imaging Experiments. In: Proceedings of the ESMRMB 2017 Barcelona, p. 315.

[36] Keil B, et al. A 64-channel 3T array coil for accelerated brain MRI. Magn. Reson. Med. 2013; 70:248-258.

[37] Noeske R, Seifert F, Rhein K H, Rinneberg H. Human Cardiac Imaging at 3T Using Phased Array Coils. Magn. Reson. Med. 2000; 44:978-82.

[38] Chung S., Kim D., Breton E., Axel L. Rapid B1+ mapping using a preconditioning RF pulse with Turbo-FLASH readout. Magn. Reson. Med., 2010; 64:439-446.

[39] Kellman P, McVeigh E. R. Image reconstruction in SNR units: a general method for SNR measurement. Magn. Reson. Med., 2005; 54:1439-1447.

[40] Winkelmann S., Schaeffter T., Koehler T., Eggers H., Doessel O. An optimal radial profile order based on the Golden Ratio for time-resolved MRI. IEEE Trans. Med. Imaging. 2007; 26:68-76.

[41] Roemer, P. B., et al., *The NMR phased array*. Magn Reson Med, 1990. 16(2): p. 192-225.

What is claimed is:

1. A coil arrangement, comprising:
at least one coil configuration having a parallel resonant circuit at a port, wherein:
the at least one coil configuration includes an inner conductor, a substrate, and an outer conductor, and the substrate being provided between the inner conductor and the outer conductor,
the at least one coil configuration is detuned by a detuning circuit configured to cause a low impedance at the port, wherein the detuning circuit includes at least one of (i) at least one positive-intrinsic-negative (PIN) diode, or (ii) at least one Micro Electronic Mechanical Systems (MEMS) switch, and
at least one of (i) the at least one PIN diode or (ii) the at least one MEMS switch is directly electrically connected to the inner conductor and the outer conductor;
wherein, during a receiving mode, two ends of the port are connected to two ends of the inner conductor.

2. The coil arrangement of claim 1, wherein the at least one coil configuration includes an inductance and a capacitance which cancel each other out.

3. The coil arrangement of claim 2, wherein the inductance and the capacitance cancel each other out such that an impedance of the coil element has no imaginary part at a working frequency.

4. The coil arrangement of claim 1, wherein the at least one coil configuration includes a loop having a distributed inductance and a distributed capacitance.

5. The coil arrangement of claim 4, wherein the distributed inductance and the distributed capacitance are formed using a coaxial structure.

6. The coil arrangement of claim 5, wherein the coaxial structure includes the inner conductor encased in the substrate wrapped with the outer conductor.

7. The coil arrangement of claim 6, wherein the coaxial structure includes at least one break in the inner conductor and the outer conductor at opposite ends thereof.

8. The coil arrangement of claim 1, wherein the at least one coil configuration is flexible.

9. The coil arrangement of claim 1, further comprising at least one pre-amplifier arrangement configured to cause the low impedance at the port.

10. The coil arrangement of claim 9, wherein the detuning circuit is at least one pre-amplifier arrangement configured to suppress currents on the at least one coil element.

11. The coil arrangement of claim 10, wherein the at least one pre-amplifier arrangement is configured to reduce inductive coupling with neighboring coil elements.

12. The coil arrangement of claim 11, wherein the pre-amplifier arrangement is configured to reduce the inductive coupling with neighboring coil elements without using a geometrical overlap.

13. The coil arrangement of claim 1, wherein the at least one coil configuration is integrated into a flexible glove.

14. The coil arrangement of claim 1, wherein the at least one coil configuration is integrated into a wearable garment.

15. The coil arrangement of claim 1, wherein the at least one coil configuration is integrated into an adaptive housing that conforms to a shape and a size of a subject being imaged.

16. The coil arrangement of claim 1, further comprising at least one pin diode configured to create the low impedance at the port.

17. The coil arrangement of claim 1, wherein the detuning circuit further includes at least one of (i) a pre-amplifier arrangement, or (ii) the MEMS switch.

18. The coil arrangement of claim 1, wherein the at least one PIN diode is directly electrically connected to the inner conductor and the outer conductor.

19. A coil arrangement, comprising:
at least one coil configuration having a parallel resonant circuit at a port,
wherein:
the at least one coil configuration has an inner conductor, a substrate and an outer conductor;
the at least one coil configuration is detuned by a detuning circuit which is configured to cause a low impedance at the port using and including at least one of (i) at least one Micro Electronic Mechanical Systems (MEMS) switch, or (ii) at least one positive-intrinsic-negative (PIN) diode;
at least one of (i) the at least one PIN diode or (ii) the at least one MEMS switch is directly electrically connected to the inner conductor and the outer conductor; and
during a receiving mode, two ends of the port are connected to two ends of the inner conductor.

20. The coil arrangement of claim 19, wherein the at least one PIN diode detunes the at least one coil configuration in a frequency range.

21. The coil arrangement of claim 19, wherein the detuning circuit comprises the at least one MEM switch.

22. The coil arrangement of claim 19, wherein the detuning circuit comprises the at least one PIN diode.

23. The coil arrangement of claim 19, wherein:
the at least one coil configuration includes an inner conductor, a substrate, and an outer conductor, the substrate being provided between the inner conductor and the outer conductor, and
the detuning circuit is coupled to the inner conductor and the outer conductor.

24. The coil arrangement of claim 19, wherein the at least one PIN diode is directly electrically connected to the inner conductor and the outer conductor.

* * * * *